US009848765B2

United States Patent
Kanagasingam et al.

(10) Patent No.: US 9,848,765 B2
(45) Date of Patent: Dec. 26, 2017

(54) QUANTIFYING A BLOOD VESSEL REFLECTION PARAMETER OF THE RETINA

(71) Applicant: COMMONWEALTH SCIENTIFIC AND INDUSTRIAL RESEARCH ORGANISATION, Campbell, Australian Capital Territory (AU)

(72) Inventors: Yogesan Kanagasingam, Floreat (AU); Alauddin Bhuiyan, Floreat (AU)

(73) Assignee: Commonwealth Scientific and Industrail Research Organisation, Campbell (AU)

( * ) Notice: Subject to any disclaimer, the term of this patent is extended or adjusted under 35 U.S.C. 154(b) by 115 days.

(21) Appl. No.: 14/903,751

(22) PCT Filed: Jul. 10, 2014

(86) PCT No.: PCT/AU2014/050118
§ 371 (c)(1),
(2) Date: Jan. 8, 2016

(87) PCT Pub. No.: WO2015/003225
PCT Pub. Date: Jan. 15, 2015

(65) Prior Publication Data
US 2016/0166141 A1  Jun. 16, 2016

(30) Foreign Application Priority Data

Jul. 10, 2013 (AU) .................................. 2013902548

(51) Int. Cl.
*A61B 3/14* (2006.01)
*A61B 3/00* (2006.01)
(Continued)

(52) U.S. Cl.
CPC .......... *A61B 3/0025* (2013.01); *A61B 3/0033* (2013.01); *A61B 3/0041* (2013.01);
(Continued)

(58) Field of Classification Search
CPC .. A61B 3/102; A61B 3/14; A61B 3/12; A61B 3/1233
(Continued)

(56) References Cited

U.S. PATENT DOCUMENTS

| 5,935,076 A | 8/1999 | Smith et al. |
| 6,305,804 B1 * | 10/2001 | Rice ..................... A61B 3/1233 351/221 |
| 2012/0177262 A1 | 7/2012 | Bhuiyan |

OTHER PUBLICATIONS

Delori, F. C., "Noninvasive Technique for Oximetry of Blood in Retinal Vessels", Applied Optics; Mar. 15, 1988, vol. 27, No. 6; pp. 1113-1125.
(Continued)

*Primary Examiner* — Hung Dang
(74) *Attorney, Agent, or Firm* — Harness, Dickey & Pierce, P.L.C.

(57) ABSTRACT

A method for quantifying a blood vessel reflection parameter associated with a biological subject, the method including, in at least one electronic processing device determining, from a fundus image of an eye of the subject, edge points of at least one blood vessel in a region near an optic disc, processing the fundus image, at least in part using the edge points, to identify blood vessel edges and central reflex edges, determining blood vessel and central reflex parameter values using the blood vessel edges and determining a blood vessel reflection parameter value at least partially indicative of blood vessel reflection using the blood vessel and central reflex parameter values.

20 Claims, 13 Drawing Sheets
(7 of 13 Drawing Sheet(s) Filed in Color)

(51) Int. Cl.
    *A61B 3/12*     (2006.01)
    *G06T 7/00*     (2017.01)
(52) U.S. Cl.
    CPC .............. *A61B 3/12* (2013.01); *A61B 3/1241* (2013.01); *G06T 7/0012* (2013.01); *G06T 2207/30041* (2013.01)
(58) Field of Classification Search
    USPC ....................................... 351/246, 206, 205
    See application file for complete search history.

(56) References Cited

OTHER PUBLICATIONS

Bankhead, P. et al., "Fast Retinal Vessel Detection and Measurement Using Wavelets and Edge Location Refinement", PLOS ONE (2012), vol. 7, No. 3, published Mar. 12, 2012 (online Journal); retrieved on Aug. 14, 2014, retrieved from the Internet: <http://www.plosone.org/article/info%3Adoi%2F10.1371%2Fjournal.pone.0032435>.
International Preliminary Report on Patentability, IB, Geneva, dated Jan. 12, 2016, incorporating the Written Opinion of the ISA, ISA/AU, Woden ACT, dated Aug. 28, 2014.

* cited by examiner

QUANTIFYING A BLOOD VESSEL REFLECTION PARAMETER OF THE RETINA

CROSS-REFERENCE TO RELATED APPLICATIONS

This application is a 371 U.S. National Stage of International Application No. PCT/AU2014/050118, filed Jul. 10, 2014, which claims priority to Australian Patent Application No. 2013902548, filed Jul. 10, 2013. The disclosures of the above applications are incorporated herein by reference.

BACKGROUND OF THE INVENTION

This invention relates to a system and method for quantifying a blood vessel reflection parameter indicative of blood vessel reflection of the retina, as well as to a biomarker for use in epidemiological diagnosis, and especially with the diagnosis of Alzheimer's disease and strokes.

DESCRIPTION OF THE PRIOR ART

The reference in this specification to any prior publication (or information derived from it), or to any matter which is known, is not and should not be taken as an acknowledgment or admission or any form of suggestion that the prior publication (or information derived from it) or known matter forms part of the common general knowledge in the field of endeavour to which this specification relates.

Retinal vessel central reflex is the bright stripe running through the centre of a blood vessel of the retina. Recent research shows its association with hypertension and the Alzheimer's diseases.

Retinal central light reflection in the surface of retinal arterioles or venules has been referred to by many descriptive terms including blood vessel wall reflection, copper-wiring, silver wiring, central arteriolar light reflex arteriolar light streak and central arteriolar light reflex. Recent research suggests that the overall increase in central reflex (CR) can be the consequence of wall thickening. This research has also shown that the ratio of vessel calibre or width and the calibre of the CR, which is hereinafter referred to as the retinal vessel reflection index (VRI), is associated with hypertension and Alzheimer diseases, along with other systemic vascular diseases, including coronary artery disease and stroke.

The assessment of arteriolar light reflex changes previously was based mainly on grader observations using direct ophthalmoscopy and was considered to be relatively subjective. An accurate and reliable CR quantification system is believed to be able to provide more information on predicting diseases with a higher degree of certainty.

SUMMARY OF THE PRESENT INVENTION

In one broad form the present invention seeks to provide a method for quantifying a blood vessel reflection parameter associated with a biological subject, the method including, in at least one electronic processing device:
  a) determining, from a fundus image of an eye of the subject, edge points of at least one blood vessel in a region near an optic disc;
  b) processing the fundus image, at least in part using the edge points, to identify blood vessel edges and central reflex edges;
  c) determining blood vessel and central reflex parameter values using the blood vessel edges; and,
  d) determining a blood vessel reflection parameter value at least partially indicative of blood vessel reflection using the blood vessel and central reflex parameter values.

Typically the blood vessel and central reflex parameter values are indicative of blood vessel and central reflex diameters respectively.

Typically the blood vessel reflection parameter is based on a ratio of the blood vessel and central reflex parameters.

Typically the region is an annular region surrounding the optic disc.

Typically the method includes:
  a) determining an optic disc location;
  b) determining an extent of the optic disc at least in part using the optic disc location; and,
  c) determining the region using the extent of the optic disc.

Typically the method includes determining the optic disc location by:
  a) displaying the at least one fundus image to a user; and,
  b) determining the optic disc location in accordance with user input commands.

Typically the method includes:
  a) displaying an indication of the region to the user; and,
  b) determining the edge points in accordance with user input commands.

Typically the method includes, processing the image by:
  a) rotating the image so that the blood vessel extends substantially across the image; and,
  b) cropping the image to remove parts of the image beyond an extent of the edge points.

Typically the method includes:
  a) identifying potential edges in the image using an edge detection algorithm;
  b) selecting edges from the potential edges using an edge selection algorithm.

Typically the method includes:
  a) identifying outer edges as blood vessel edges; and,
  b) determining edges between the blood vessel edges to be potential central reflex edges.

Typically the method includes selecting central reflex edges from the potential central reflex edges based on changes in image intensity.

Typically the method includes:
  a) determining a plurality of blood vessel and central reflex diameters using the blood vessel and central reflex edges; and,
  b) determining the blood vessel and central reflex parameter values using the plurality of blood vessel and central reflex diameters.

Typically the method includes determining the plurality of blood vessel and central reflex diameters using opposite edge points of edge pixel pairs.

Typically the method includes, determining the blood vessel and central reflex parameter values by at least one of:
  a) selecting a minimum diameter; and,
  b) determining an average diameter.

Typically the method includes, determining a blood vessel profile using blood vessel reflection parameter values for a plurality of blood vessels in the region.

Typically at least one of a blood vessel reflection parameter value and a blood vessel profile are used as a biomarker for predicting at least one of:
  a) vascular disease;
  b) cerebrovascular disease;

c) APOE ϵ4 status; and,
d) Alzheimer's disease.

Typically the method includes at least one of:
a) receiving the fundus image from a fundus camera;
b) receiving the fundus image from a remote computer system via a communications network; and,
c) retrieving the fundus image from a database.

In one broad form the present invention seeks to provide apparatus for quantifying a blood vessel reflection parameter associated with a biological subject, the apparatus including at least one electronic processing device that:
a) determines, from a fundus image of an eye of the subject, edge points of at least one blood vessel in a region near an optic disc;
b) processes the at least one image, at least in part using the edge points, to identify blood vessel edges and central reflex edges;
c) determines blood vessel and central reflex parameter values using the blood vessel edges; and,
d) determines a blood vessel reflection parameter value at least partially indicative of blood vessel reflection using the blood vessel and central reflex parameter values.

In one broad form the present invention seeks to provide a method for quantifying blood vessel reflection associated with the retina comprising:
a) selecting edge start-points of a suitable blood vessel around the optic disc area of a digital image of the eye, fundus to constitute the edge start points for grading calculations;
b) automatically region cropping to create a cropped digital image around the edge start points and translating the cropped digital image to create a resultant image appropriately orientated for processing;
c) processing the resultant image digitally to obtain blood vessel edge and central reflex edge information from the identified vessel edges; and
d) measuring the calibres of the outer edges of the blood vessel and the central reflex from the edge information.

The method typically includes calculating the vessel reflection index being the ratio of the blood vessel calibre and the central reflex calibre to constitute a biomarker for predicting vascular disease of a patient.

In one broad form the present invention seeks to provide a blood vessel quantification system for quantify blood vessel reflection associated with the retina comprising:
a) a user interface for enabling an analyst to interact with the system;
b) an optic disc (OD) selection process for automatically computing an OD area and a vessel selection (VS) area after the analyst defines the OD centre on the digital image of the fundus using the user interface;
c) a mapping, processing and measuring (MPM) process including:
   i) an image region selection process for automatically mapping a proximal region around vessel edge start-points and obtaining a selected image for subsequent processing;
   ii) an edge detection and profiling process for automatically processing the selected image to obtain and map the vessel, edge and central reflex edge profiles;
   iii) an edge selection process for automatically selecting vessel edges and central reflex edges closest to the vessel edge start-points to calculate the calibre of the outer vessel edges and the central reflex edges; and
   iv) a vessel, reflection index measurement process for automatically calculating the vessel refection index of the selected vessel;
      wherein the MPM process includes a vessel edge selection process for interactively functioning with the analyst via the user interface to enable the analyst to set the vessel edge start-points from within the VS area after the OD selection process has completed computing the VS area for the MPM process to proceed with performing the aforementioned automated processes.

Typically the user interface includes a module to allow an analyst to select an image file containing a digital image of the fundus of the eye of a patient, and enter relevant reference data for subsequent processing by the system.

Typically the user interface includes an image loading process for uploading a selected image file.

It will be appreciated that the broad forms of the invention and their respective features can be used in conjunction or interchangeably and reference to separate inventions is not intended to be limiting.

BRIEF DESCRIPTION OF THE DRAWINGS

This patent or patent application contains at least one drawing executed in color. Copies of this patent or patent application publication with color drawing(s) will be provided by the Office upon request and payment of the necessary fee.

An example of the present invention will now be described with reference to the accompanying drawings, in which:—

DETAILED DESCRIPTION OF THE PREFERRED EMBODIMENTS

Figure 1:
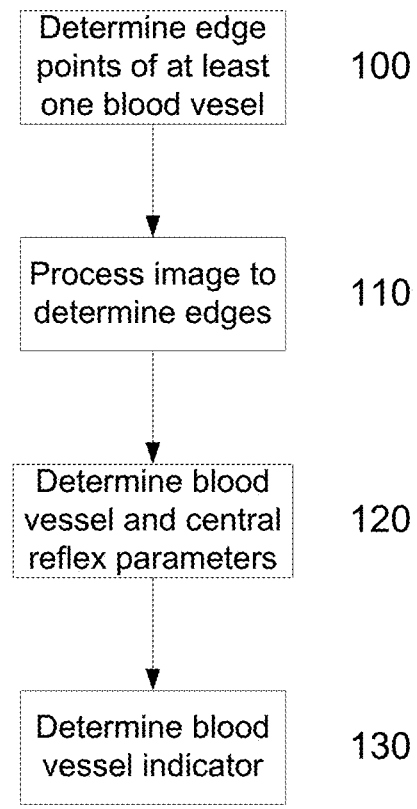
FIG. 1 is a flow chart of an example of a process for quantifying a blood vessel reflection parameter associated with a retina of a biological subject.

An example of a method for quantifying a blood vessel reflection parameter associated with a retina of a biological subject will now be described with reference to FIG. 1.

For the purpose of example, it is assumed that the process is performed at least in part using one or more electronic processing devices, for example forming part of a computer or other processing system, which may be a stand-alone processing system, or part of a cloud or server based architecture, as will be described in more detail below.

In this example, at step 100 edge points of at least one blood vessel in a region near an optic disc are determined from a fundus image of an eye of the subject. The edge points can be determined in any one of a number of ways and this could involve utilising automated edge detection techniques. Alternatively, due to the difficulty in accurately identifying blood vessel edges within fundus images, the edge points can be determined at least partially in accordance with input commands provided by a user, such as an eye care specialist, retinal image grader, image analyst, or the like. The edge points typically correspond to outer edges of the blood vessel, and this will be used for the purpose of illustration for the remainder of the specification unless otherwise indicated. However, alternatively, the edge points could be taken to be the boundary between the central reflex and the blood vessel, which may be preferred in the event that these are easier to visually distinguish in the fundus images, in which case the following method will be adapted accordingly.

At step 110 the fundus image is processed at least in part using the edge points, to identify blood vessel edges and central reflex edges. This could be achieved in any manner, but in one example involves utilising edge detection techniques to identify edges within the images, which can then be subsequently identified as blood vessel or central reflex edges. As part of this process, the edge points can be utilised as guides to detect blood vessel edges, whilst central reflex edges are identified as edges located between the blood vessel edges.

At step 120 blood vessel and central reflex parameter values are determined using the blood vessel and central reflex edges. The parameter values typically correspond to widths of the blood vessel and central reflex respectively, and these can be determined in any appropriate manner. For example, this can involve taking multiple width measurements along a length section of the blood vessel and central reflex, and then selecting parameter values based on one or more of these width measurements.

At step 130 a value for a blood vessel reflection parameter is determined using the blood vessel and central reflex parameter values. The blood vessel reflection parameter value is at least partially indicative of blood vessel reflection and is typically suitable for use as a biomarker of one or more biological conditions. The nature of the blood vessel reflection parameter and the manner in which this is determined may vary depending upon the preferred implementation and the nature of the condition being identified. For example, a ratio of the blood vessel and central reflex widths (or vice versa) can be utilised as an indicator of Alzheimer's disease, whereas different indicators can be used for other conditions such as vascular disease.

Accordingly, the above-described example provides a straightforward mechanism for allowing a blood vessel reflection parameter to be quantified based on blood vessel or central reflex edge points identified within fundus images, with these being subsequently used to identify blood vessel and central reflex edges. This approach improves the reliability and accuracy of the detection process ensuring the resulting vessel indicator is sufficiently accurately determined to allow it to be used as a biomarker for use in diagnosing the presence, absence or degree of one or more biological conditions.

A number of further features will now be described.

As mentioned above, in one example, the blood vessel and central reflex parameter values are indicative of blood vessel and central reflex diameters or widths respectively, although other measurements could be used depending on the condition being assessed. Additionally, the blood vessel reflection parameter is typically based on a ratio of the blood vessel and central reflex parameters, although it will be appreciated that alternative indicators could be used as required.

Typically the region is an annular region surrounding the optic disc. An annular region surrounding the optic disc is chosen as the blood vessels are more clearly defined and hence can be measured more accurately than in other regions of the retinal fundus image, although it will be appreciated that other regions could be used in addition to or as an alternative to an annular region around the optic disc.

In one example, the method includes determining an optic disc location, determining an extent of the optic disc, at least in part using the optic disc location, and then determining the region using the extent of the optic disc. This can be achieved in any appropriate manner, and could be achieved using manual or automated processes, or a combination of the two.

Assuming however that manual techniques are used, the method typically includes displaying at least one fundus image to a user and then determining the optic disc location in accordance with user input commands. Thus, the user identifies the position, which could include a single location or region, based on visual inspection of the image, and then identifies this using a mouse or other input device. Following this thresholding techniques can be used to examine the intensity and/or colour of the fundus image, to therefore identify an edge and hence extent of the optic disc, with the region being identified based on the size of the optic disc. For example, the region can be an annular region having a width based on a proportion of the diameter of the disc, as described in more detail below. It will also be appreciated, however, that automated optic disc identification techniques can be used.

Once the optic disc and hence the region have been ascertained, the process typically includes displaying an indication of the region to the user and then determining edge points in accordance with user input commands. Thus, this process involves displaying the region to the user so the user can accurately identify edge points of a blood vessel located within the region. Alternatively, this could be performed using an automated edge detection technique, or through a combination of manual and automated processes, for example by having the processing system identify potential edge points, and have these reviewed and confirmed by an user.

The image can be processed in any appropriate manner in order to allow the blood vessel and central reflex edges to be more accurately identified. Typically this includes removing extraneous regions of the image to reduce image processing requirements and/or to allow manipulation of image properties to aid edge detection. For example, this can include altering the contrast, saturation, brightness or intensity of the image to more clearly highlight the blood vessel and central reflex locations.

In one particular example, processing of the image is achieved by rotating the image so that the blood vessel extends substantially across the image and then cropping the image to remove parts of the image beyond an extent defined by the edge points. Thus, the edge points in effect act as a boundary for the image, so that the image is limited to parts of the blood vessel within a perimeter defined by the edge points. Furthermore, the image is rotated so that the subsequent edge detection processes can be limited to features extending laterally or transversely across the image, which are more likely to correspond to edges, which further reduces the computational requirements of the image processing technique.

In one example, the method includes identifying potential edges in the image using an edge detection algorithm and then selecting edges from the potential edges using an edge selection algorithm. Thus, a two-stage process is utilised in order to identify potential edges and then select those which correspond to blood vessel and central reflex edges. For example, as part of this process, the method, can include identifying outer edges as blood vessel edges and determining edges between the blood vessel edges to be potential central reflex edges. The processing system will then determine a number of potential central reflex edges and if only two are identified, these are determined to be central reflex edges. Otherwise further processing can be performed, for example based on changes in image intensity, to identify those potential central reflex edges that actually correspond to central reflex edges.

The method typically includes determining a plurality of blood vessel and central reflex diameters (or widths) using the blood vessel and central reflex edges and then determining the blood vessel and central reflex parameter values using the plurality of blood vessel and central reflex diameters. This could include, for example, determining an average diameter, selecting a minimum diameter, or the like. The diameters are typically determined using opposite edge points of edge pixel pairs, as will be described in more detail below.

In one example, the method includes determining a blood vessel profile using blood vessel reflection parameter values for a plurality of blood vessels within the region. This can include blood vessels of a single type but may also include different types of blood vessel. Thus, in one example, this could include determining arteriolar to venular blood vessels and then determining the profile based on a ratio or other combination of these values.

In one example, at least one of the blood vessel reflection parameter values and blood vessel profile are used as a biomarker for predicting either vascular disease of a patient and/or Alzheimer's disease and examples of this will be described in more detail below.

In one example, the method comprises selecting edge start-points of a suitable blood vessel around the optic disc area of a digital image of the eye fundus to constitute the edge start points for grading calculations, automatically region cropping to create a cropped digital image around the edge start points and translating the cropped digital image to create a resultant image appropriately orientated for processing, processing the resultant image digitally to obtain blood vessel edge and central reflex edge information from the identified vessel edges and measuring the calibres of the outer edges of the blood vessel and the central reflex from the edge information.

The vessel reflection index can then be based on the ratio of the blood vessel calibre and the central reflex calibre to constitute a biomarker for predicting vascular disease of a patient.

A blood vessel quantification system can also be provided for quantifying blood vessel reflection associated with the retina. In this case, the system includes a user interface for enabling an analyst to interact with the system; an optic disc (OD) selection process for automatically computing an OD area and a vessel selection (VS) area after the analyst defines the OD centre on the digital image of the fundus using the user interface and a mapping, processing and measuring (MPM) process. The MPM process typically includes an image region selection process for automatically mapping a proximal region around vessel edge start-points and obtaining a selected image for subsequent processing, an edge detection and profiling process for automatically processing the selected image to obtain and map the vessel edge and central reflex edge profiles, an edge selection process for automatically selecting vessel edges and central reflex edges closest to the vessel edge start-points to calculate the calibre of the outer vessel edges and the central reflex edges and a vessel reflection index measurement process for automatically calculating the vessel refection index of the selected vessel. In this case, the MPM process includes a vessel edge selection process for interactively functioning with the analyst via the user interface to enable the analyst to set the vessel edge start-points from within the VS area after the OD selection process has completed computing the VS area for the MPM process to precede with performing the aforementioned automated processes.

In one example, the user interface can include a module to allow an analyst to select an image file containing a digital image of the fundus of the eye of a patient, and enter relevant reference data for subsequent processing by the system. The user interface can also include an image loading process for uploading a selected image file.

Figure 2:
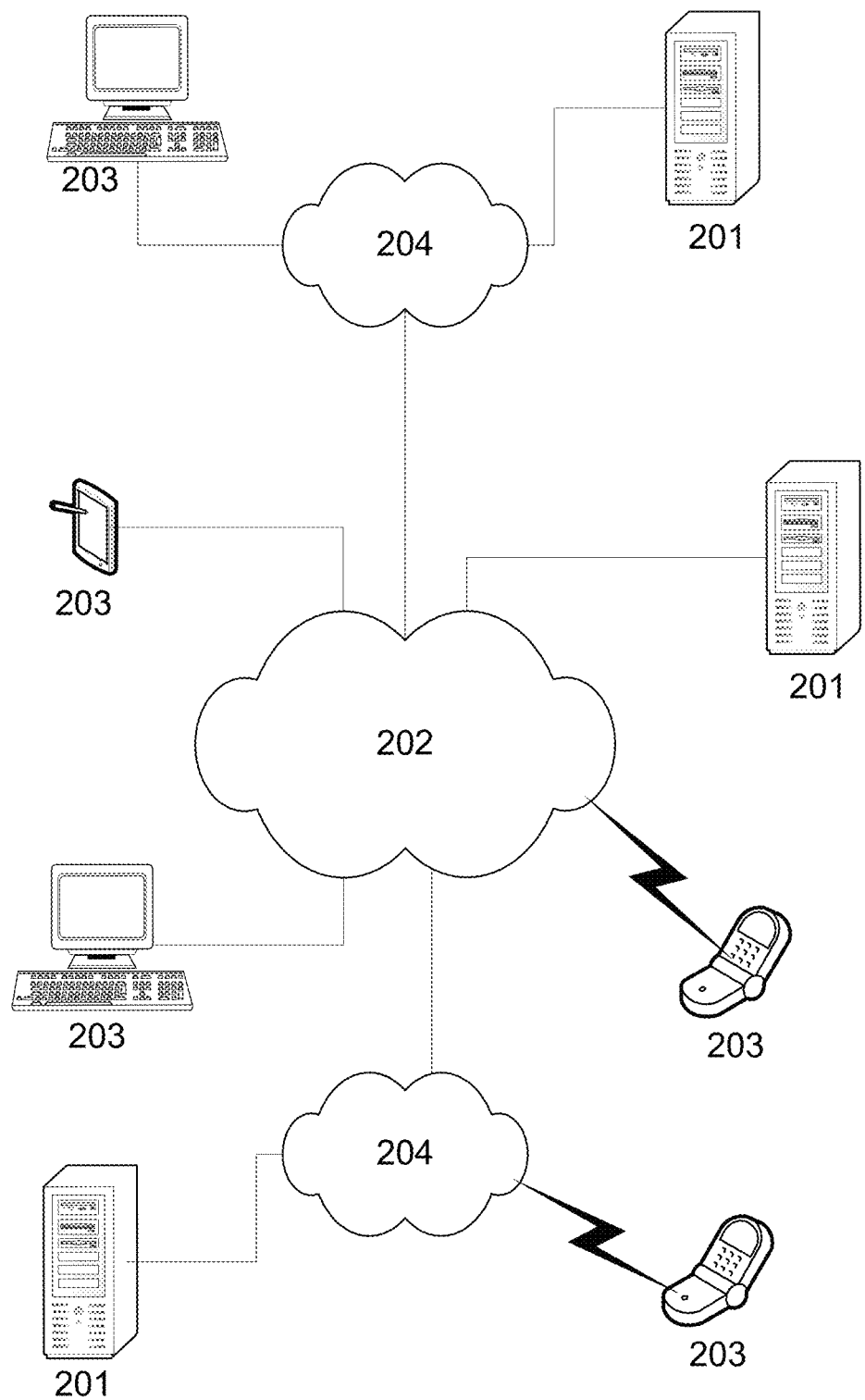
FIG. 2 is a schematic diagram of an example of a distributed computer architecture.

As part of the above-described process, the fundus image can be acquired from a subject using a fundus camera, or alternatively could be received from a remote computer system via a communications network or retrieved from a database. Thus, it will be appreciated from this that a range of different computer architectures could be used and examples of these will now be described in further detail with reference to FIG. 2.

In this example, a base station 201 is coupled via a communications network, such as the Internet 202, and/or a number of local area networks (LANs) 204, to a number of computer systems 203. It will be appreciated that the configuration of the networks 202, 204 are for the purpose of example only, and in practice the base station 201 and computer systems 203 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, the base station 201 includes one or more processing systems 210 coupled to a database 211. The base station 201 is adapted to be used in performing the analysis of the image data including reviewing the subject data selecting an analysis process and providing results of the analysis. The computer systems 203 are typically adapted to communicate with the base station 201, allowing image and/or subject data to be provided and to allow details of indicator values or notifications to be received. Additionally, the computer systems can be adapted to allow video conferencing to be performed for example to allow for remote consultation with a specialist.

Whilst the base station 201 is a shown as a single entity, it will be appreciated that the base station 201 can be distributed over a number of geographically separate locations, for example by using processing systems 210 and/or databases 211 that are provided as part of a cloud based environment. It will also be appreciated that the above described arrangement is not essential and other suitable configurations could be used.

Figure 3:
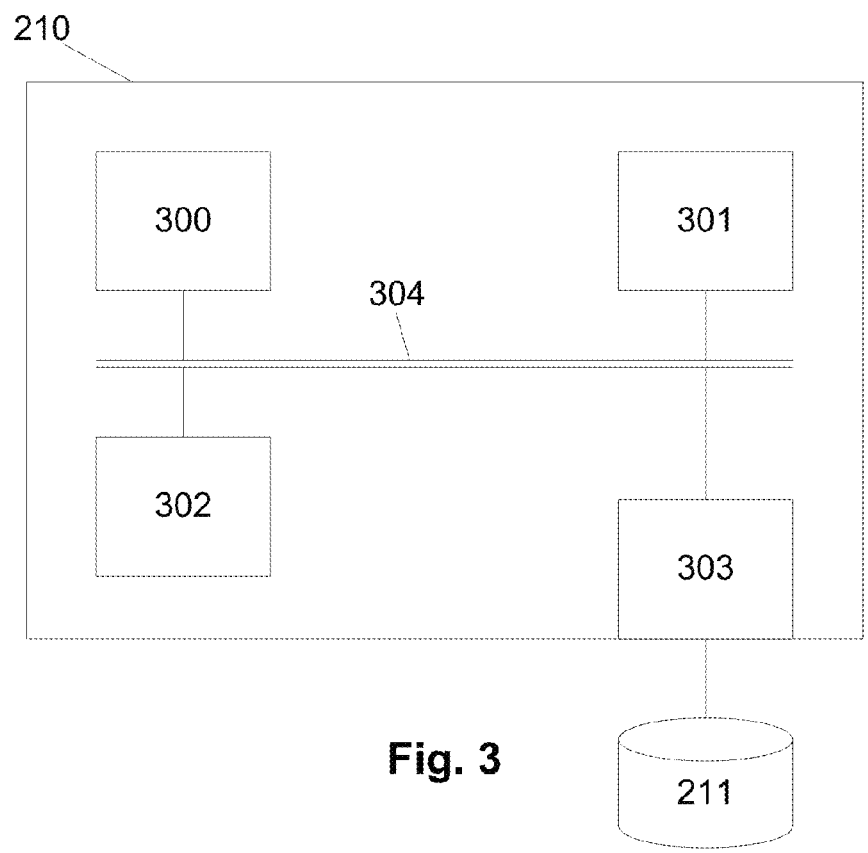
FIG. 3 is a schematic diagram of an example of a processing system of FIG. 2.

An example of a suitable processing system 210 is shown in FIG. 3. In this example, the processing system 210 includes at least one microprocessor 300, a memory 301, an optional input/output device 302, such as a keyboard and/or display, and an external interface 303, interconnected via a bus 304 as shown. In this example the external interface 303 can be utilised for connecting the processing system 210 to peripheral devices, such as the communications networks 202, 204, databases 211, other storage devices, or the like. Although a single external interface 303 is shown, this is for the purpose of example only, and in practice multiple interfaces using various methods (eg. Ethernet, serial, USB, wireless or the like) may be provided.

In use, the microprocessor 300 executes instructions in the form of applications software stored in the memory 301 to allow the analysis process and any other associated tasks to be performed. The applications software may include one or more software modules, and may be executed in a suitable execution environment, such as an operating system environment, or the like, and specific examples will be described in more detail below.

Accordingly, it will be appreciated that the processing system 210 may be formed from any suitable processing system, such as a suitably programmed computer system, PC, web server, network server, or the like. In one particular example, the processing system 210 is a standard processing system such as Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 4:
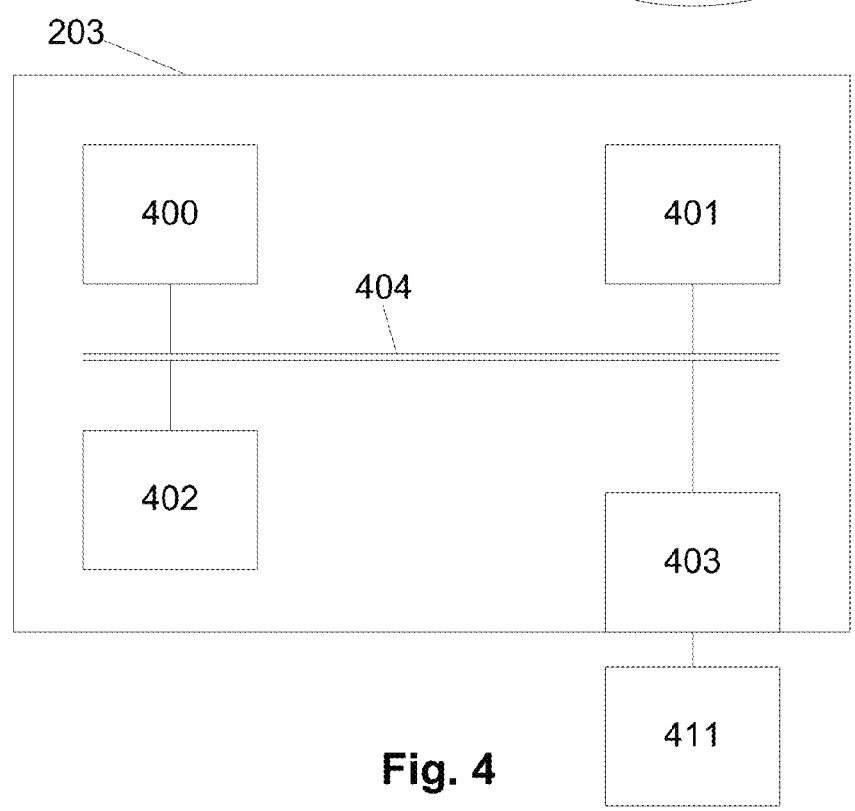
FIG. 4 is a schematic diagram of an example of a computer system of FIG. 2.

As shown in FIG. 4, in one example, the computer system 203 includes at least one microprocessor 400, a memory 401, an input/output device 402, such as a keyboard and/or display, and an external interface 403, interconnected via a bus 404 as shown. In this example the external interface 403 can be utilised for connecting the computer system 203 to peripheral devices, such as the communications networks 202, 204, one or more imaging devices 411, such as a fundus camera, external storage devices, or the like. Although a single external interface 403 is shown, this is for the purpose of example only and in practice multiple interfaces using various methods (eg. Ethernet, serial, USB, wireless or the like) may be provided.

In use, the microprocessor 400 executes instructions in the form of applications software stored in the memory 401 to allow communication with the base station 201, for example to allow fundus images to be uploaded thereto and transferred to the base station 201 for analysis, and/or to perform the analysis locally on the computer system 203.

Accordingly, it will be appreciated that the computer systems 203 may be formed from any suitable processing system, such as a suitably programmed PC, Internet terminal, lap-top, hand-held PC, smart phone, PDA, web server, or the like. Thus, in one example, the processing system 210 is a standard processing system such as Intel Architecture based processing system, which executes software applications stored on non-volatile (e.g., hard disk) storage, although this is not essential. However, it will also be understood that the computer systems 203 can be any electronic processing device such as a microprocessor, microchip processor, logic gate configuration, firmware optionally associated with implementing logic such as an FPGA (Field Programmable Gate Array), or any other electronic device, system or arrangement.

Further examples of the analysis process will now be described in further detail. For the purpose of these examples, it is assumed that the processing system 210 of the base station 201 typically executes applications software, with actions performed by the processing system 210 being performed by the processor 300 in accordance with instructions stored as applications software in the memory 301 and/or input commands received from a user via the I/O device 302, or commands received from the computer system 203.

It will also be assumed that the user interacts with the processing system 210 via a GUI (Graphical User Interface), or the like presented on the computer system 203. Actions performed by the computer system 203 are performed by the processor 401 in accordance with instructions stored as applications software in the memory 402 and/or input commands received from a user via the I/O device 403.

However, it will be appreciated that the above described configuration assumed for the purpose of the following examples is not essential, and numerous other configurations may be used. It will also be appreciated that the partitioning of functionality between the computer systems 203, and the base station 201 may vary, depending on the particular implementation, such as performing the process on the computer system 203 as a stand-alone computer system.

Figure 5A:
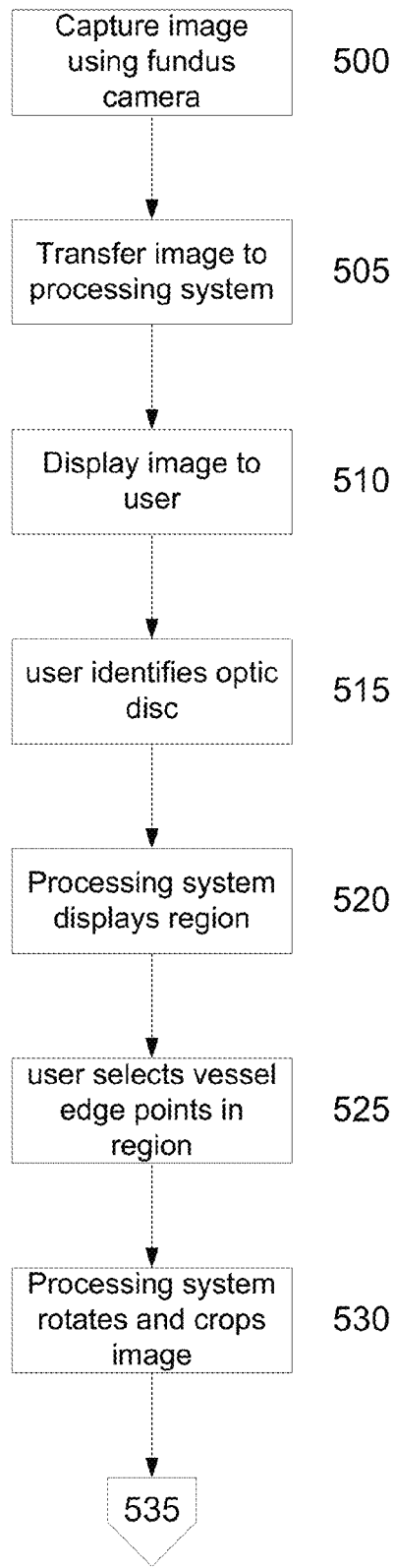
FIGS. 5A and 5B are a flow chart of a further example of a for quantifying a blood vessel reflection parameter associated with a retina of a biological subject.
Figure 5B:
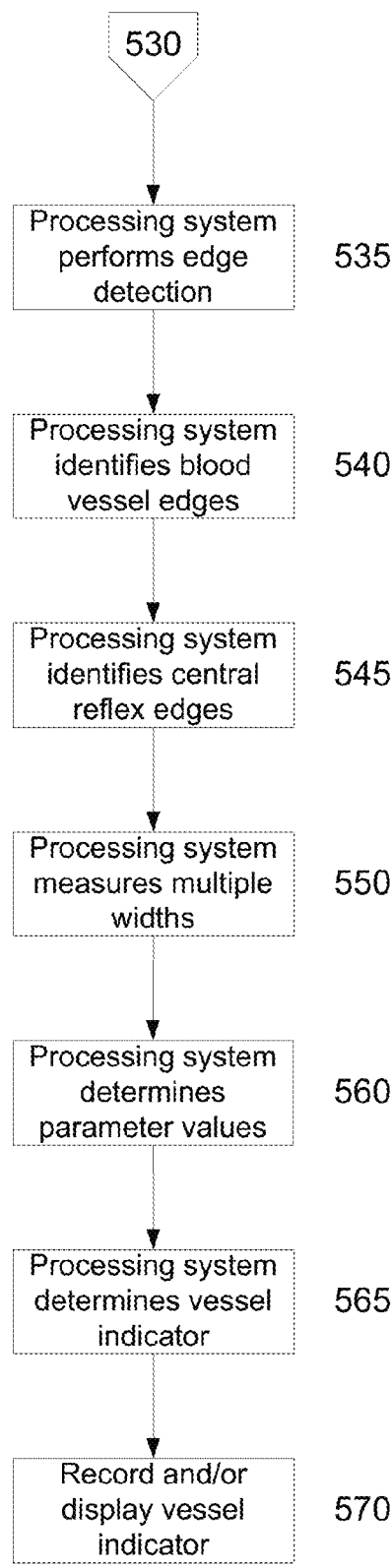

A second example will now be described with reference to FIGS. 5A and 5B.

In this example, at step 500 a fundus image is captured using a fundus camera 411 with this being transferred via the computer system 203 to the processing system 210, at step 505. At step 510 the fundus image is displayed, for example via a browser application, or custom user interface, to an user allowing the user to identify a location of the optic disc at step 515. This will typically involve allowing the user to highlight the optic disc location utilising a mouse or other similar input device.

Figure 6A:
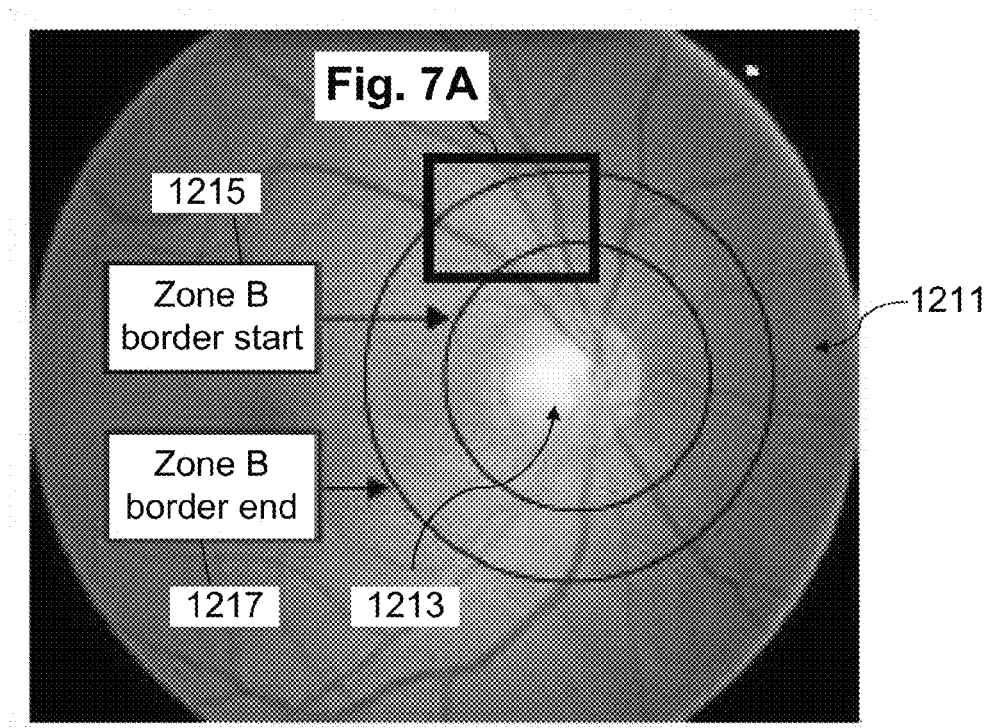
FIG. 6A is a rendered perspective view of a retinal image showing the optic disc area and the location of a cropped image of the vessel region from which a blood vessel is selected for the grading process in colour.
Figure 6B:
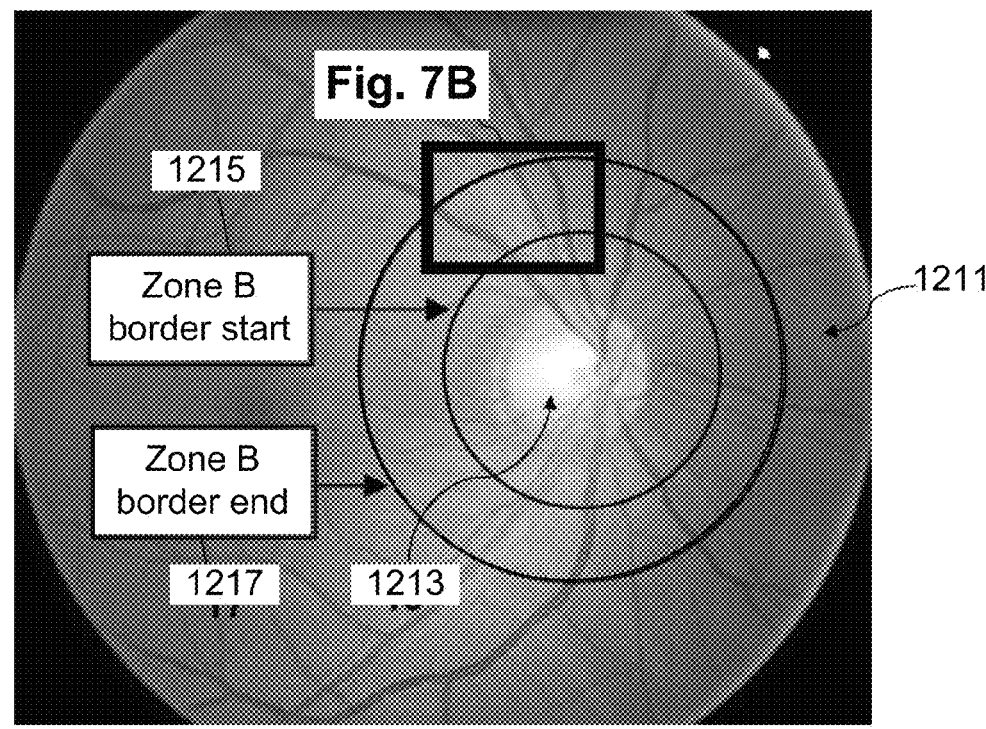
FIG. 6B is the same view in grey scale.

At step 520, the processing system 210 calculates and displays a region to the user. The region is typically an annular region extending around the optic disc and an example of this is shown in FIG. 6A, in which the optic disc is shown at 613 with the region being defined by the boundaries 615, 617.

At step 525 the user selects vessel edge points within the region. It will be appreciated as part of this that the user may be able to manipulate the image, for example, to zoom in on particular blood vessels, and optionally alter the contrast, brightness, hue, saturation or other image properties, to allow the blood vessels edges to be more easily discerned.

Figure 10A:
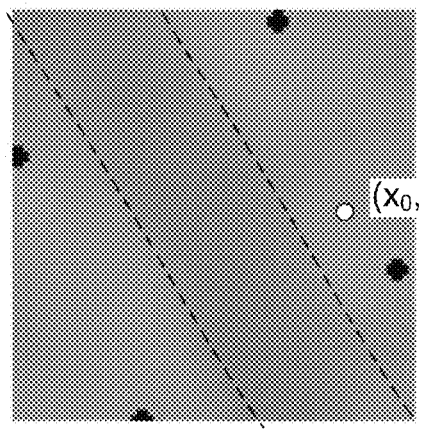
FIGS. 10A, 10C and 10E are a series of images showing diagrammatically how a cropped region is selected, rotated and then cut to obtain the vessel region from which measurements are made in colour.
Figure 10B:
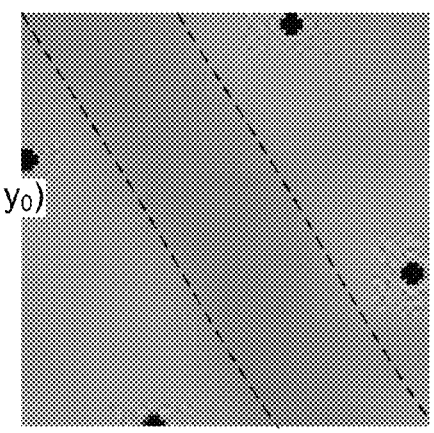
FIGS. 10B, 10D and 10F are the same views in grey scale.
Figure 10C:
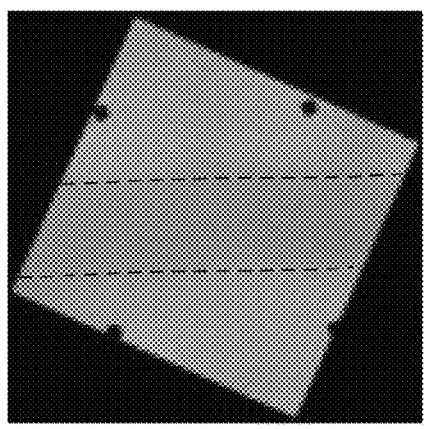
Figure 10D:
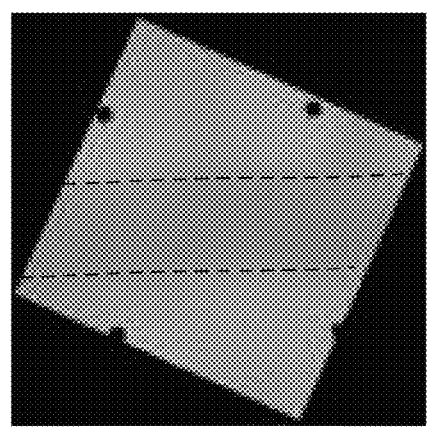
Figure 10E:
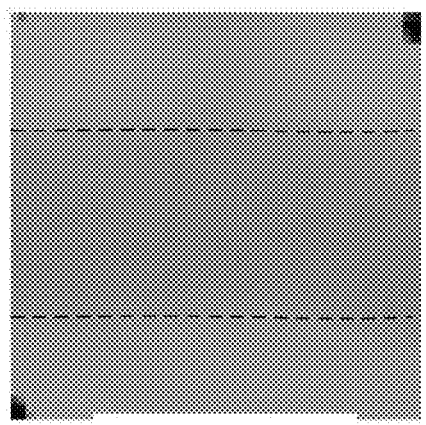
Figure 10F:
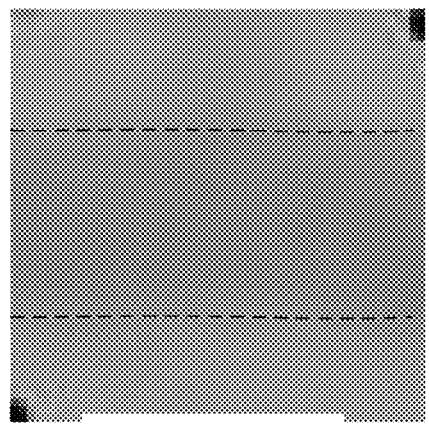
Figure 11A:
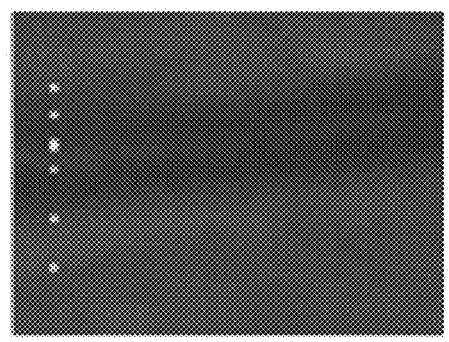
FIG. 11A to 11D are a series of images showing how the vessel and CR edges are selected and reduced in the cropped image to arrive at a final vessel selection for VRI measurement.
Figure 11B:
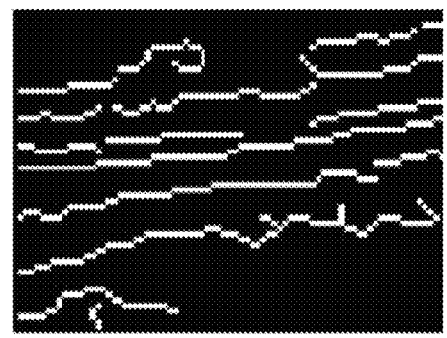
Figure 11C:
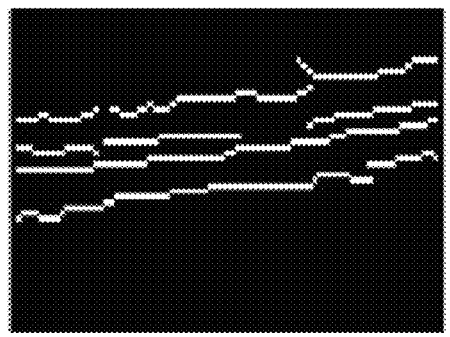
Figure 11D:
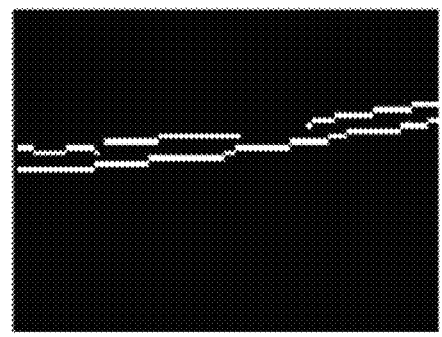
Figure 12:
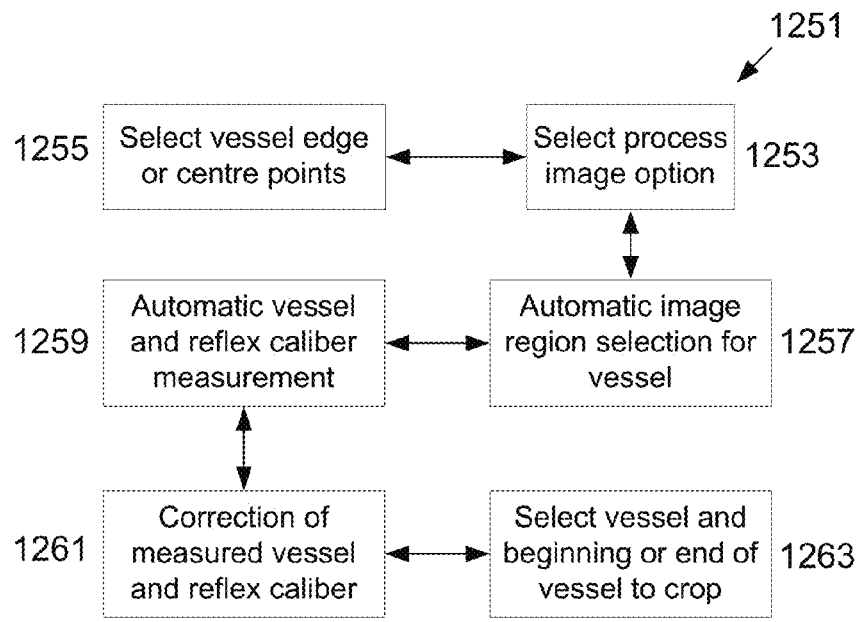
FIG. 12 is a block diagram of the synthesising software of the retinal blood vessel quantification system and method.

At step 530, the processing system rotates 210 and crops the image so that the blood vessel extends horizontally across the image and fills the image. An example of this is shown in FIGS. 10A, 10C and 10E, as will be described in more detail below.

At step 535 the processing system 210 performs edge detection, using this to identify blood vessel edges at step 540, typically on the basis of the outermost edges within the cropped and rotated image. At step 545 the processing system 210 determines central reflex edges typically by defining any edges between the blood vessel edges to be central reflex edges, as will be described in more detail below.

At step 550 the processing system 210 measures multiple widths both for the central reflex and blood vessel, widths. This is typically achieved by measuring between the outermost edges of edge pixels at multiple different locations along the length of the blood vessel segment contained within the cropped image. This is then utilised in order to determine blood vessel and central reflex parameter values, which are typically based on the minimum width measured for each of the blood vessel and central reflex respectively.

At step 565 the processing system can then determine a vessel indicator with this being stored or displayed to the user at step 570 thereby allowing this to be used an ocular biomarker.

A further example usage of the system will now be described. In this regard, this example is directed towards a retinal blood vessel quantification system and method using computer software to perform a grading of selected blood vessels of the retina of a patient using a retinal blood vessel reflection index.

Figure 7A:
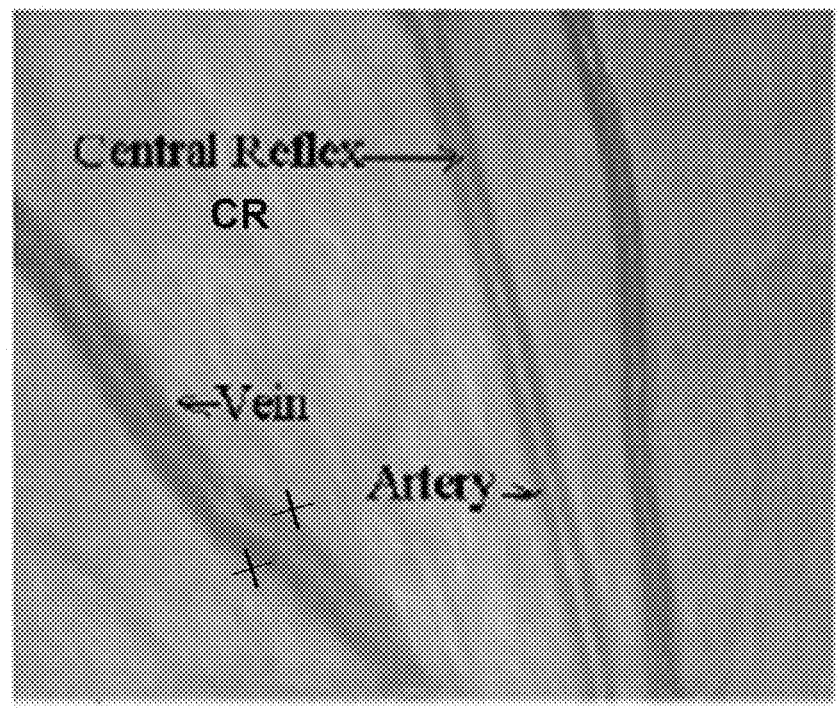
FIG. 7A is a cropped image of the vessel region shown in FIG. 6A, which image shows a retinal artery, vein and the central reflex of both, which are selected to be the subject of the grading process in colour.
Figure 7B:
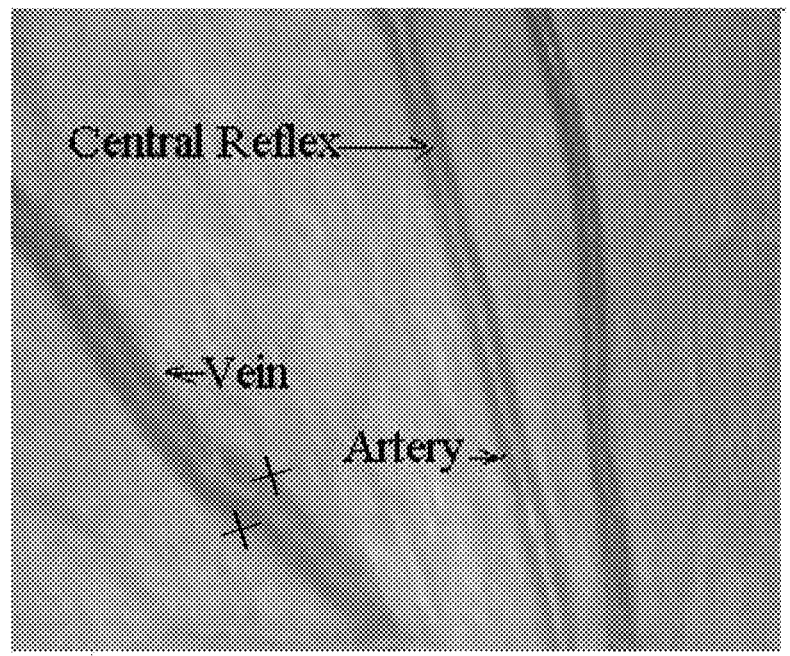
FIG. 7B is the same view in grey scale.

In broad terms, the method is implemented using software which uses a grader's interaction to determine vessel edge points and then computes the edges based on a region growing process and measures the vessel and central reflex width and their ratio. The vessel detection method relies on the optic disc (OD) centre for finding vessel direction and orientation, which are used to identify the vessel region mapping. The OD centre is also used to map a region for central reflex quantification, which is in turn used to determine a retinal vessel reflection index (VRI), which is the ratio of the vessel calibre or width and the calibre of the bright stripe running through the centre of the vessel. The bright stripe is known as the central reflex (CR) and is best shown in FIG. 7A. In this regard, research shows that the VRI is associated with hypertension, stroke, Alzheimer's and other vascular diseases and thus the quantification of such can provide a biomarker for identifying such diseases in a patient.

Figure 8:
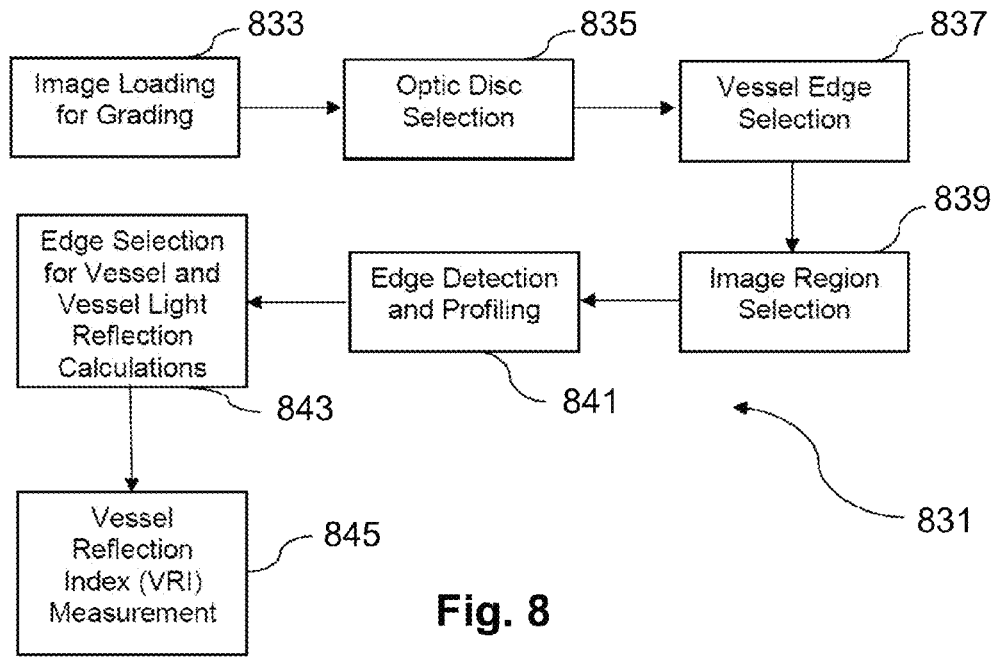
FIG. 8 is a flow chart showing the overall method for VRI measurement.
Figure 9:
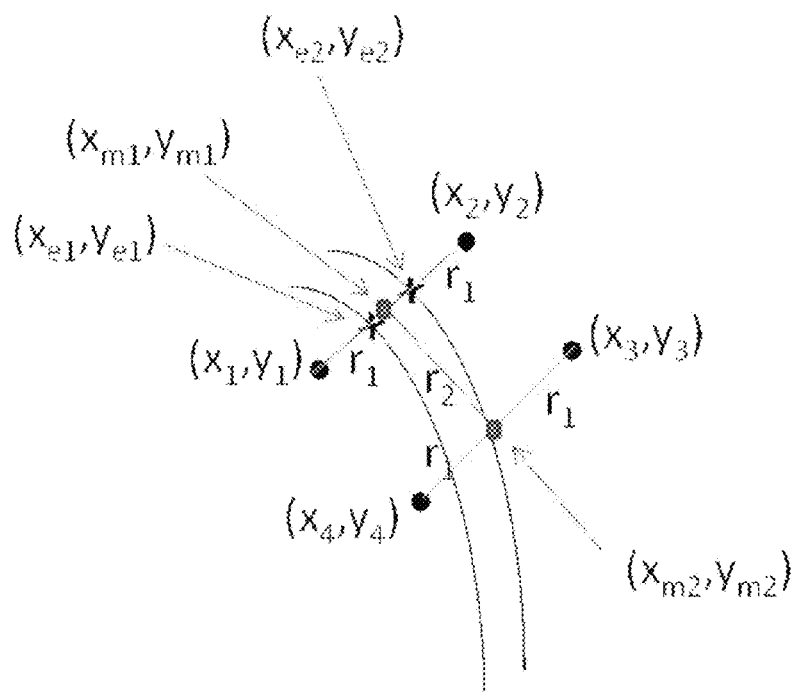
FIG. 9 is a schematic diagram showing how the image region is obtained and extracted from the digital image of the eye fundus.

The process 31 by which the quantification is performed in general terms is shown in FIG. 8 and is described with reference to FIGS. 9 and 10.

In this regard, a digital colour image 811 taken of the fundus of the eye of a patient, the fundus including the retina 813, is loaded at step 833 by the system from a directory of image files stored in a library to be accessed by the system. An optic disc (OD) area, Zone A, is defined in the image at step 835 along with a vessel selection (VS) area, Zone B, which is a frusto-conical area of the fundus circumscribing the OD area. As shown in FIG. 6A, the OD area is that area including the bright and white area of the retina 613 and the VS area is a predefined area around Zone A from which a retinal blood vessel is selected from the image. Zone B is used for selecting retinal blood vessels for analysis, as this region is close to the retina in the OD area, and provides better delineation of the outer edges of arterial and venular blood vessels and their CR than does the OD area. As shown, VS area is arbitrarily circumscribed by the superposed circular lines 615 and 617 which define its boundaries.

As shown in FIG. 7A, two diametrically opposite outer edge start points X-X are then identified at the outer edges of the selected blood vessel at step 837, with the CR disposed in between these outer edges.

This step forms part of an overall vessel area mapping, processing and measuring MPM) process which is performed automatically by an image region step 839, an edge detection and profiling step 841 and an edge selection for vessel and vessel light refection calculation step 843, after the analyst completes selecting the vessel edges for analysis at step 835. Essentially the blood vessel calibre between the outer edge start points X-X and the CR calibre defined between two inner outer edges of the CR intersecting with the diametral plane extending between the edge start-points is digitally mapped and processed so that the calibres of the blood vessel and CR are measured. From these measurements, outputs are produced for the blood vessel calibre, the vessel CR calibre and the VRI is ultimately calculated at step 845, being the ratio of the vessel calibre to CR calibre.

Moreover, once the vessel edge points are selected, the method automatically finds the vessel region to be graded by region cropping as shown in FIG. 7A. The vessel and central reflex edge information is then obtained from the resultant image. The vessel and central reflex calibre is then calculated to produce the output results.

In the preferred embodiment, the retinal blood vessel quantification process is performed semi-automatically in order to obtain best results, partly involving direction and instruction by the analyst and partly by the fully automated vessel region mapping process. The entire process is guided by software 1251 comprising discrete software modules including user interface modules 1253 and 1255 to allow the analyst to perform the initial selection steps and then invoke the vessel region mapping process which is synthesised by automated modules 1257 and 1259 that progress to fine tuning calculating modules 1261 and 1263 that also involve a user interface to complete the VRI measurement.

Now describing the overall process 831 and software 1251 in more detail, an analyst initially invokes a main routine implemented as part of the computer software of the retinal blood vessel quantification system, which allows the analyst to optionally invoke the user interface modules 1253 and 1255. By way of these user interface modules, the analyst is able to interact with the system, select an image file containing a digital image of the fundus of the eye of a patient, enter relevant reference data and select edge start-points of a suitable blood vessel around the optic disc.

The main routine includes a menu process that initially presents an analyst user of the system with an option to enter a directory of image files containing digital colour images of the fundus of the eye of various patients requiring analysis via the user interface.

On the analyst selecting a particular image file of a patient, an image loading process is invoked at step 833, which is synthesised by the Select 'Process Image' Option module 1253. The module allows the analyst to upload a selected image file for analysis using an OD selection process, which is invoked at step 835 and synthesised by the Select Vessel Edge or Centre Point module 1255. The OD selection process automatically computes the OD area, Zone A, and the VS area, Zone B, at step 835 using the OD centre and radiuses therefrom, after the analyst identifies the OD centre. Moreover, Zone B is calculated as the frusto-conical region starting at 1.5*OD diameter and ending at 2.5*OD diameter, as measured from the OD-centre in the retinal image. The optic disc itself is selected using a CR grading interface. This interface allows the analyst to interact with the system to enable considered selection of the OD rather than automated selection, which is more error prone.

However, alternatively, the OD can be determined automatically. This can be achieved using any suitable process such as thresholding the brightness or intensity of pixels and identifying features having a disc shape. This can be achieved using any suitable technique, such as region growing or the like. In one example, this is achieved using a 4-quadrant disc detection method which examines quadrants in the vicinity of determined OD.

In more detail, this can be achieved using OD size, shape and colour information to detect the OD in the image. Firstly, the method automatically determines the threshold intensity value by approximating the OD area information in each image and using this number to select the maximum intensity levels from the image histogram. Secondly, using this threshold value, the potential OD area is selected from the image. Following this, the Region Growing Technique is applied in the thresholded image to identify the potential OD regions. Finally, the Hough circle detection algorithm is applied in the gradient image based on the potential OD regions to identify the OD and compute its centre and radius.

Once the OD selection process has defined the Zone A and Zone B areas, the software routine progresses to the MPM process, which commences with invoking a vessel edge selection process at step 837 also synthesised by the user interface module 1255. The vessel edge selection process displays a coloured image of the Zone B area, and includes navigation tools for the analyst to zoom in and out and around the image, and edge point setting means to allow the analyst to select the vessel edge start-points from within the Zone B area on the displayed image. This is best shown in FIG. 7A, where a vein is selected and vessel edge start-points are set at X-X.

In the present embodiment, the edge start-points are set at not a particularly well delineated area of the vessel to demonstrate the power of the mapping, processing and measuring algorithms of the MPM process.

Once the vessel edge start-points are set by the analyst, the analyst invokes an image region selection process at step 839 and synthesised by the Automatic Image Region Selection for Individual Vessel module 1257 to automatically select the proximal region around the vessel edge start-points for analysis by the MPM process. The process performed by the image region selection process is best described with reference to FIG. 15 of the drawings, which is a schematic diagram. Essentially, the process involves cropping a proximal region around the outer edge start-points to create a selected image, so that only the selected image of the vessel is processed. The proximal region to be cut from the overall digital image of the eye fundus is selected by approximating the vessel centreline by drawing a perpendicular line in the imaginary line between the edge start-points, considering the OD centre to compute the orientation of the blood vessel and calculating the boundary points of the image to be cut. The cut image is then rotated to align the blood vessel horizontally and the resultant image is then cropped to obtain the selected image for subsequent processing.

More particularly, the two outer edge start-points of the blood vessel selected by the user art represented as $(x_{e1}, y_{e1})$ and $(x_{e2}, y_{e2})$. From these two points, the image region selection process maps the boundary points $(x_1, y_1), (x_2, y_2), (x_3, y_3)$ and $(x_4, y_4)$ as shown in FIG. 9.

This is done by calculating the centre point $(x_{m1}, y_{m1})$ of the edge start-points where $x_{m1}=(x_{e1}+x_{e2})/2$ and $y_{m1}=(y_{e1}+y_{e2})/2$. This centre point is used to map the other centre point $(x_{m2}, y_{m2})$ which together will become the centre points of a cropped image that will be subsequently generated and profiled by an edge detection and profiling process at step 41. These centre points are approximated to be the two centreline points of the vessel, whereby the goal is to map the vessel and CR in the centre of the cropped image.

The second centre point $(x_{m2}, y_{m2})$ is obtained using the slope $\theta$ of the two edge start-points $(x_{e1}, y_{e1})$ and $(x_{e2}, y_{e2})$ and $r_2$ being the normal distance of the first centre point $(x_{m1}, y_{m1})$. The direction of the second centre point is computed based on the OD centre $(c_x, c_y)$, i.e. the same direction from the OD to the first centre point. It is also necessary to define the image quadrant in order to get the actual vessel directional information in the image. The OD centre $(c_x, c_y)$ is used to compute the actual position or real slope of the edge point centreline as follows:

$\theta=\theta+\pi/2$ if $x_{e1}<=c_x$ and $x_{e2}<=c_x$ $\theta=\theta+3\pi/2$ if $x_{e1}>=c_x$ and $x_{e2}>=c_x$ $\theta=\theta+\pi/2$ if $y_{e1}>=c_y$ and $y_{e2}>=c_y$ and $\theta<0$ $\theta=\theta+3\pi/2$ if $y_{e1}>=c_y$ and $y_{e2}>=c_y$ and $\theta>0$ $\theta=\theta+\pi/2$ if $y_{e1}<=c_y$ and $y_{e2}<=c_y$ and $\theta>0$ $\theta=\theta+3\pi/2$ if $y_{e1}<=c_y$ and $y_{e2}<=c_y$ and $\theta<0$ \hfill (1)

Following this, the slope of the centreline is computed as $\theta=\theta+\pi/2$ i.e. perpendicular to the line between the edge start-points. Then the second centre point $(x_{m2}, y_{m2})$ is obtained as follows:

$x_{m2}=x_{m1}+r_2*\cos(\theta)$ $y_{m2}=y_{m1}+r_2*\sin(\theta)$ \hfill (2)

Once the two centreline points are obtained, they are used to determine line end points for mapping four boundary points to crop the region from the image. For this the slope $\theta_c$ of the line that consists of the two centreline points is used with Equation 3 to obtain the boundary points.

$x_1=x_{m1}+r_1*\cos(\theta_c+3\pi/2); y_1=y_{m1}-r_1*\sin(\theta_c+3\pi/2)$ $x_2=x_{m1}+r_1*\cos(\theta_c\pi/2); y_2=y_{m1}-r_1*\sin(\theta_c+\pi/2)$ $x_3=x_{m2}+r_1*\cos(\theta_c\pi/2); y_3=y_{m2}-r_1*\sin(\theta_c+\pi/2)$ $x_4=x_{m2}+r_1*\cos(\theta_c+3\pi/2); y_4=y_{m2}-r_1*\sin(\theta_c+3\pi/2)$ \hfill (3)

Thus when the analyst selects the edge start-points of the blood vessel, the process calculates the centreline points and only needs to compute the centreline slope $\theta_c$ and obtain the quadrant information to map the actual slope and obtain the boundary points.

Once the coordinates of the cropped image are obtained, the image is processed with a fine translation so that the vessel position can be obtained and aligned horizontally in the centre of the image. This provides freedom to determine the edges of the vessel with confidence. To do this, the coordinates of the cropped image are translated with respect to an imaginary axis ($x_o$, $y_o$) about the centre of the cropped image using Equation 5. The coordinates of the origin are defined using Equation 4.

$$x_o = x_{min} + (x_{max} - x_{min})/2 \text{ and}$$

$$y_o = y_{min} + (x_{max} - x_{min})/2 \quad (4)$$

$$x_{1t} = x_1 - x_o; \quad y_{1t} = y_1 - y_o$$

$$x_{2t} = x_2 - x_o; \quad y_{2t} = y_2 - y_o$$

$$x_{3t} = x_3 - x_o; \quad y_{3t} = y_3 - y_o$$

$$x_{4t} = x_4 - x_o; \quad y_{4t} = y_4 - y_o \quad (5)$$

Graphically, the process is shown in FIGS. 10A, 100 and 10E, with approximate extents of the CR being shown in dotted lines. After translation of the image coordinates to create the cut image at FIG. 10A, the image is rotated at FIG. 10C to align the blood vessel shown by the dark hue horizontally within the cut image, and the vessel end that is closer to the OD is positioned at the left side of the rotated image to arrive at the appropriately orientated image at FIG. 10C. The angle of rotation ($\theta$) is defined using Equations 6 to 9 as follows:

$$\theta_1 = \arctan\left(-\frac{x_3 - x_1}{x_3 - x_1}\right) \quad (6)$$

Case 1: $\theta_1 > 0$ (7)

$$\theta_r = \begin{cases} \theta_1 + 2\pi & \text{if } x_3 \geq x_1 \ \& \ y_3 \geq y_1 \\ \theta_1 + \pi & \text{Otherwise} \end{cases}.$$

Case 2: $\theta_1 < 0$ (8)

$$\theta_r = \begin{cases} \theta_1 + \pi & \text{if } x_3 \geq x_1 \ \& \ y_3 \leq y_1 \\ \theta_1 & \text{Otherwise} \end{cases}.$$

Case 3: $\theta_1 = 0$ (9)

$$\theta_r = \theta_1$$

The rotated coordinates of the translated points are defined using Equation 10. The height and width of the rotated image is represented by $noX_{rimg}$ and $noY_{rimg}$ respectively.

$$x_{1tr} = \sin(-\theta) * y_{1t} - \cos(-\theta) * x_{1t}; \quad y_{1tr} = \cos(-\theta) * y_{1t} + \sin(-\theta) * x_{1t} \quad (10)$$

$$x_{2tr} = \sin(-\theta) * y_{2t} - \cos(-\theta) * x_{2t}; \quad y_{2tr} = \cos(-\theta) * y_{2t} + \sin(-\theta) * x_{2t}$$

$$x_{3tr} = \sin(-\theta) * y_{3t} - \cos(-\theta) * x_{3t}; \quad y_{3tr} = \cos(-\theta) * y_{3t} + \sin(-\theta) * x_{3t}$$

$$x_{4tr} = \sin(-\theta) * y_{4t} - \cos(-\theta) * x_{4t}; \quad y_{4tr} = \cos(-\theta) * y_{4t} + \sin(-\theta) * x_{4t}$$

The boundary points of the translated and rotated image are defined using Equation 11 and the region cropped as shown in FIG. 10C 10E to arrive at the selected image. The cropping of the rotated image for blood vessel detection is defined using Equation 12.

$$x_{1n} = \lceil (noX_{rimg}/2 - x_{1tr}) \rceil; \quad y_{1n} = \lceil (noY_{rimg}/2 + y_{1tr}) \rceil \quad (11)$$

$$x_{2n} = \lceil (noX_{rimg}/2 - x_{2tr}) \rceil; \quad y_{2n} = \lceil (noY_{rimg}/2 + y_{2tr}) \rceil$$

$$x_{3n} = \lceil (noX_{rimg}/2 - x_{3tr}) \rceil; \quad y_{3n} = \lceil (noY_{rimg}/2 + y_{3tr}) \rceil$$

$$x_{4n} = \lceil (noX_{rimg}/2 - x_{4tr}) \rceil; \quad y_{4n} = \lceil (noY_{rimg}/2 + y_{4tr}) \rceil$$

-continued $$regX_{min} = \min(x_{1n}, x_{2n}, x_{3n}, x_{4n}); \ regY_{min} = \min(y_{1n}, y_{2n}, y_{3n}, y_{4n}) \quad (12)$$

$$regX_{max} = \max(x_{1n}, x_{2n}, x_{3n}, x_{4n}); \ regY_{max} = \max(y_{1n}, y_{2n}, y_{3n}, y_{4n})$$

Once the selected image is obtained using the image region selection process an edge detection and profiling process is invoked at step 841 and synthesised by the Automatic Vessel and Reflex Calibre Measurement module 1259 to select the outer edge of the blood vessel and the CR edges within the blood vessel. The edge detection and profiling process uses a Canny edge detection operation to extract the edges to be used for blood vessel and central reflex calibre measurements. The concept of the Canny edge detection operation is explained in the publication Digital Image Processing, $3^{rd}$ edition by R. C. Gonzalez and R. Woods, published by Pearson Prentice Hall, 2008 (Gonzalez & Woods) and the paper of J. Canny entitled Ä computational approach to edge detection" published by IEEE Trans. In Pattern Analysis and Machine Intelligence, Vol. 8(6), pp. 679-698, 1986 (Canny). Both publications Gonzalez & Wood and Canny are incorporated herein by reference.

In the edge transaction and profiling process performed at step 841 the threshold value of the canny edge is set to obtain 10% of the pixels as edge pixels. Once the edges are obtained in this manner, a pruning operation is applied so that the unwanted branches (due to noise) in the edge are removed. Each vessel edge-pixels are mapped by applying a region growing operation as also explained in Gonzalez & Woods, and junction points are computed to determine a vessel edge. Each of the edge pixels are checked that have more than two segments with a length of at least two pixels. For any segment length having less than 5 pixels, the segment is removed from the edge.

After all of the potential edges of the blood vessel are detected, the MPM process progresses to invoking an edge selection (ES) process for selecting the vessel and vessel light reflection edges at step 843. In the ES process, the edges that are closest to the selected vessel edge start-points identified in the beginning are used for vessel and region selection. The middle edge(s) are considered to be CR or vessel reflection edges. If there are more than two edges in between the vessel edges, then their profile is computed as if they are a first edge and a second edge. For this edge pixel intensity levels are considered at each side of an edge. For example, going from top to bottom of the image region, if the average intensity level is moving from low to high, it will be considered as a second edge and vice versa. In this manner, the edges for multiple first edges and second edges can be removed. Whilst performing this process, the distance of the CR or vessel reflection edges and the outer edges of the blood vessel are checked and the pair which is of a similar distance is selected. FIGS. 11A to 11D show graphically how the process progresses to identify the outer edges of the blood vessel at FIG. 11C and the edges of the CR or vessel refection at FIG. 11D.

Alternatively, this could be achieved using a Gaussian derivative operation to extract the edges for vessel and central reflex. The Gaussian first derivative user returns a bell-shaped distribution in the intensity profile (i.e., gradient magnitude) along the edge vertical cross-section. For edge start-point selection this pattern is considered while traversing through a column from low to high in row number. Any pixel's is checked to determine if its gradient magnitude is higher or equal to its vertical neighbours. This follows the $2^{nd}$ pixel above and below in row of the current pixel. A region growing method is applied traversing toward the higher column number and selecting the pixels which have value greater than or equal to the current pixel. If all the values are lower than the current pixel we select the closest one.

Once the blood vessel and CR or inner reflection edges are obtained, the MPM process finally invokes a VRI measurement process at step 845, which is synthesised by the Grader Correction on the Measured Vessel and Reflex Calibre module 1261. This VRI measurement process combines and computes the width of the vessel at different cross-section positions using the Euclidian distance between opposite edge points of pixel pairs. The shortest distance is selected as the width of that particular cross-section. For example, the $5^{th}$ edge point can be used for measuring the width of the $5^3$ cross-section. The edge pixel positions occurring at cross-sections 1, 2, 3, 4, 5, 6, 7, 8, 9, 10, 11 are then combined with the same positions in the opposite edge using different permutations and combinations to arrive at a calculated width for each cross-section. That is the pixel in position 1 for edge 1 is combined with all 11 pixel positions at edge 2, same for pixel position 2 and so on. As a consequence of this, the shortest distance in these combinations is determined to be the width of the vessels for the $5^{th}$ cross-section. This approach is adopted to compute all of the cross-sectional widths of the vessel being the outer vessel width and the CR width.

Once the cross-sectional widths are obtained, the VRI measurement process proceeds to calculate the VRI for the particular vessel.

The aforementioned process can be repeated for obtaining the VRI of many vessels or at different vessel locations of the fundus image using the Select Vessel and Begin or End of a Vessel to Crop the Vessel Part module 1263 to build up a VRI profile for the particular patient, which can be used as a biomarker for identifying whether there is a high or low risk of vascular disease.

Although the preferred embodiment has been described as obtaining the VRI for retinal blood vessels generally, in another embodiment, the main focus of the retinal blood vessel quantification system is to measure the retinal arteriolar wall to lumen ratio to arrive at a VRI profile for the patient for predicting the patient's predisposition or propensity towards Alzheimer's disease.

The method works with selecting the arterial edge points rather than venular edge points to achieve the highest precision. Importantly, the system is user driven and so must return a value of retinal VRI if there is some evidence of vessel reflection as determined by the user. Thus the system works on the basis of knowing that there is vessel reflection as selected by the analyst and calculates it with forced finding of the features indicating same.

Furthermore, whilst the preferred embodiment has been described with a user interface permitting the analyst to select edge points of a suitable blood vessel around the OD area of the image of the eye fundus manually, other embodiments of the invention use synthesising software to automatically select such edge points and thus provide a fully automated blood vessel quantification system and method.

It should be appreciated that the scope of the present invention is not limited to the particular embodiments described herein. Other embodiments may be envisaged that apply the invention to predicting other diseases than those mentioned and other types of blood vessels.

To investigate the effectiveness of the above described technique, a study was performed using 150 optic disc-centered digital retinal photographs from 150 subjects from a population-based cross-sectional study persons aged 40 to 80 years. The above described techniques were used to quantify retinal arteriolar central light reflex (CR) by selecting vessel edge points semi-automatically and then automatically computing the CR, vessel diameter, and the CR to the vessel diameter ratio (CRR). Reliability was assessed using intra-class correlation coefficient (ICC) and Bland-Altman Plots, Multiple linear regression analyses were performed to assess the associations between CRR and systemic and ocular factors to further validate the proposed software.

Statistical analyses were conducted using the SPSS Statistics software. Three approaches were used for reliability assessment using intra-class correlation coefficients (ICC): 1) intra-grader reliability, 2) inter-grader reliability and 3) intra-visit repeatability for CRR measures. For intra-grader reliability assessment of the system, the same images were graded by two individual graders. For inter-grader reliability grading, the same image is graded by the same grader at two different sessions. For intra-visit repeatability, two images were graded by the same grader which were taken at baseline and follow up visits. The intra- and inter-grader reliability, of CRR measurement were assessed using 24 retinal photographs and the intra-visit repeatability of CRR measurement was assessed using 21 paired retinal photographs. Careful attention was given by graders to measure the same vessel locations. Reliability was assessed by intra-class correlation coefficient and Bland-Altman plots.

150 participants were included for final analysis of CRR and mean arteriolar blood pressure. Univariate and multiple linear regression models were performed to examine the relationship of CRR with systemic factors. Factors significant at $p<0.1$ with CRR from univariate analysis and potential confounders (age & gender) were included in the multiple regression model.

The mean (SD) age of participants was 58.71 yr (7.8), mean systolic blood pressure 87.72 (30.74) mmHg, the diastolic blood pressure 81.52 (13.77) mmHg. The prevalence rate of hypertension (systolic blood pressure more than 80 mmHg, the diastolic blood pressure more than 90 mmHg) in these subjects was 36.7%.

Figure 13A:
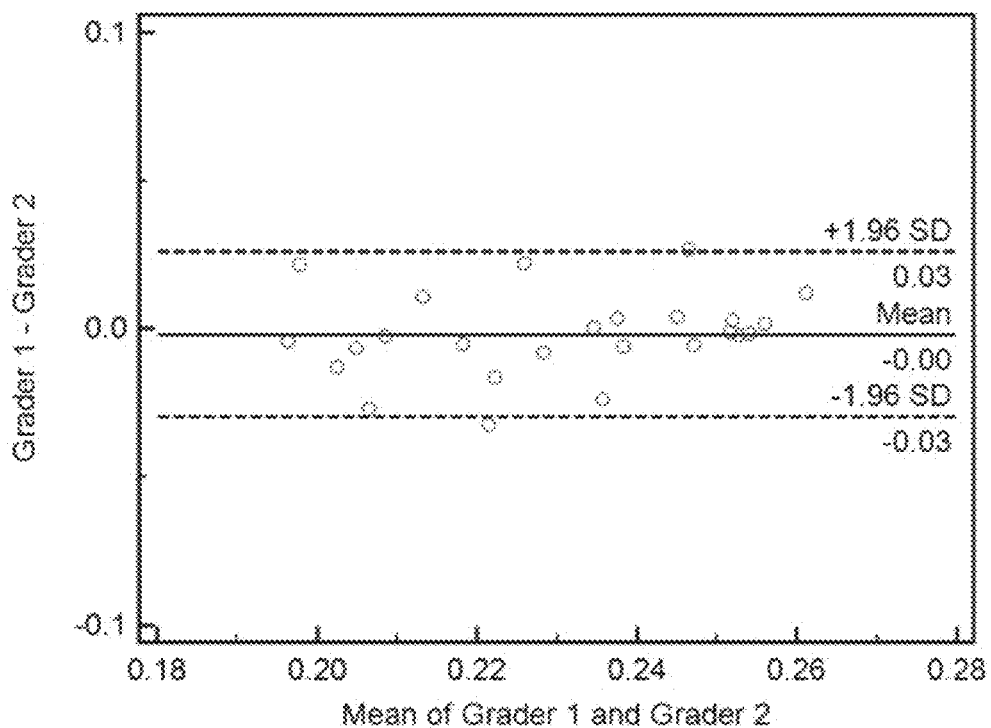
FIGS. 13A to 13C are Bland Altman plots showing inter-grader agreement, intra-grader agreement and intra-visit agreement, respectively.
Figure 13B:
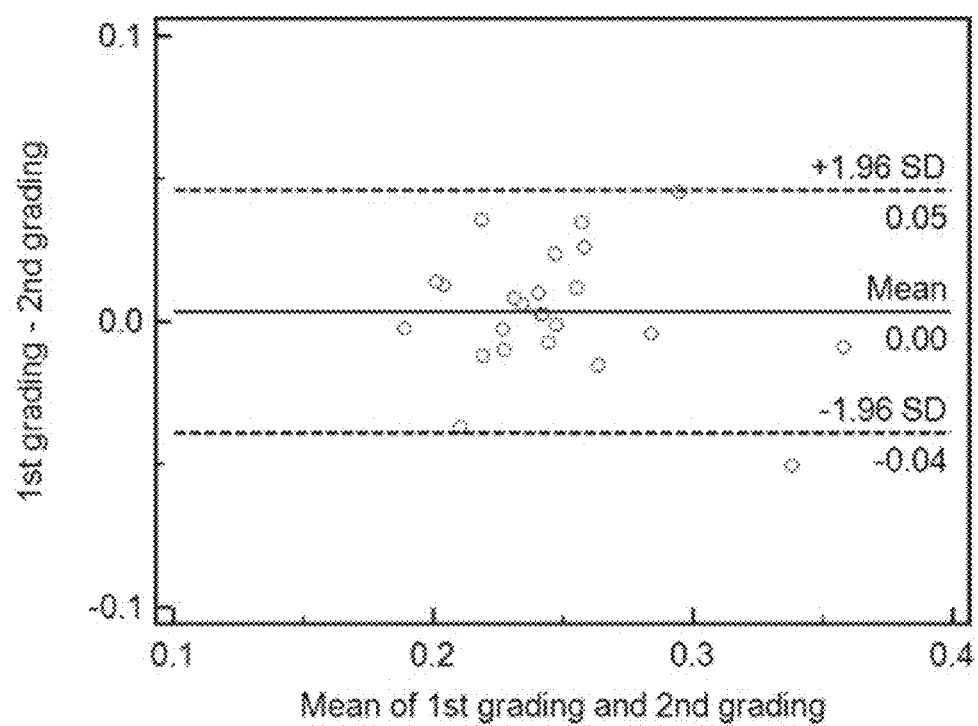
Figure 13C:
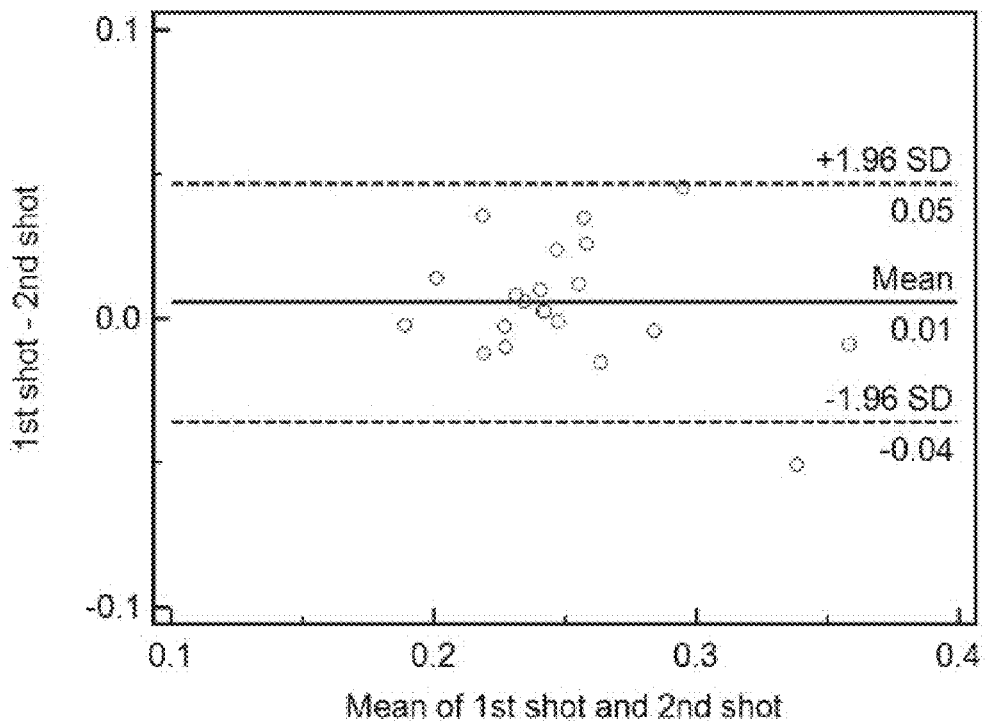

The intra-grader and inter-grader reliability analysis for CRR computation is shown in Table 1. ICC was high for inter-grader, intra-grader reliability and intra-visit repeatability which were 0.78, 0.86 and 0.87, respectively. FIGS. 13A to 13C show Bland-Altman plots depicting the inter-grader agreement, intra-grader agreement and intra-visit agreement for CRR.

TABLE 1

|  | ICC | (95% CI) |
| --- | --- | --- |
| Intra-grader reliability (n = 24) | 0.86 | (0.71 to 0.94) |
| Inter-grader reliability (n = 25) | 0.78 | (0.56 to 0.90) |
| Intra-visit repeatability (n = 21) | 0.87 | (0.71 to 0.95) |

This highlights a high degree of agreement, meaning the above described techniques provide a mechanism for reliably assessing CRR in subjects, even when using different users. This, in turn means that the techniques can be deployed widely whilst maintaining a high degree of accuracy in resulting indicator values and hence diagnosis of conditions.

Table 2 shows univariate analysis between systemic and ocular factors with CRR measurement. Systolic blood pressure, diastolic blood pressure, mean arterial blood pressure, body mass index, C-reactive protein level and presence of opacification were significantly associated with CRR.

TABLE 2

| | Pearson correlation coefficient, r | p-value |
|---|---|---|
| Age | 0.077 | 0.361 |
| Gender | 0.126 | 0.134 |
| Systolic blood pressure | 0.412 | <0.001 |
| Diastolic blood pressure | 0.419 | <0.001 |
| Mean arterial blood pressure | 0.444 | <0.001 |
| Body mass index | 0.207 | 0.013 |
| Blood Glucose | 0.87 | 0.083 |
| Total cholesterol | 0.029 | 0.730 |
| LDL cholesterol | −0.019 | 0.828 |
| HDL cholesterol | −0.053 | 0.530 |
| Diabetes | 0.096 | 0.253 |
| Logarithm of C-Reactive Protein | 0.169 | 0.047 |
| Spherical equivalent | −0.159 | 0.058 |
| Intraocular pressure | 0.041 | 0.630 |
| Any opacification | 0.298 | <0.001 |

Figure 14:
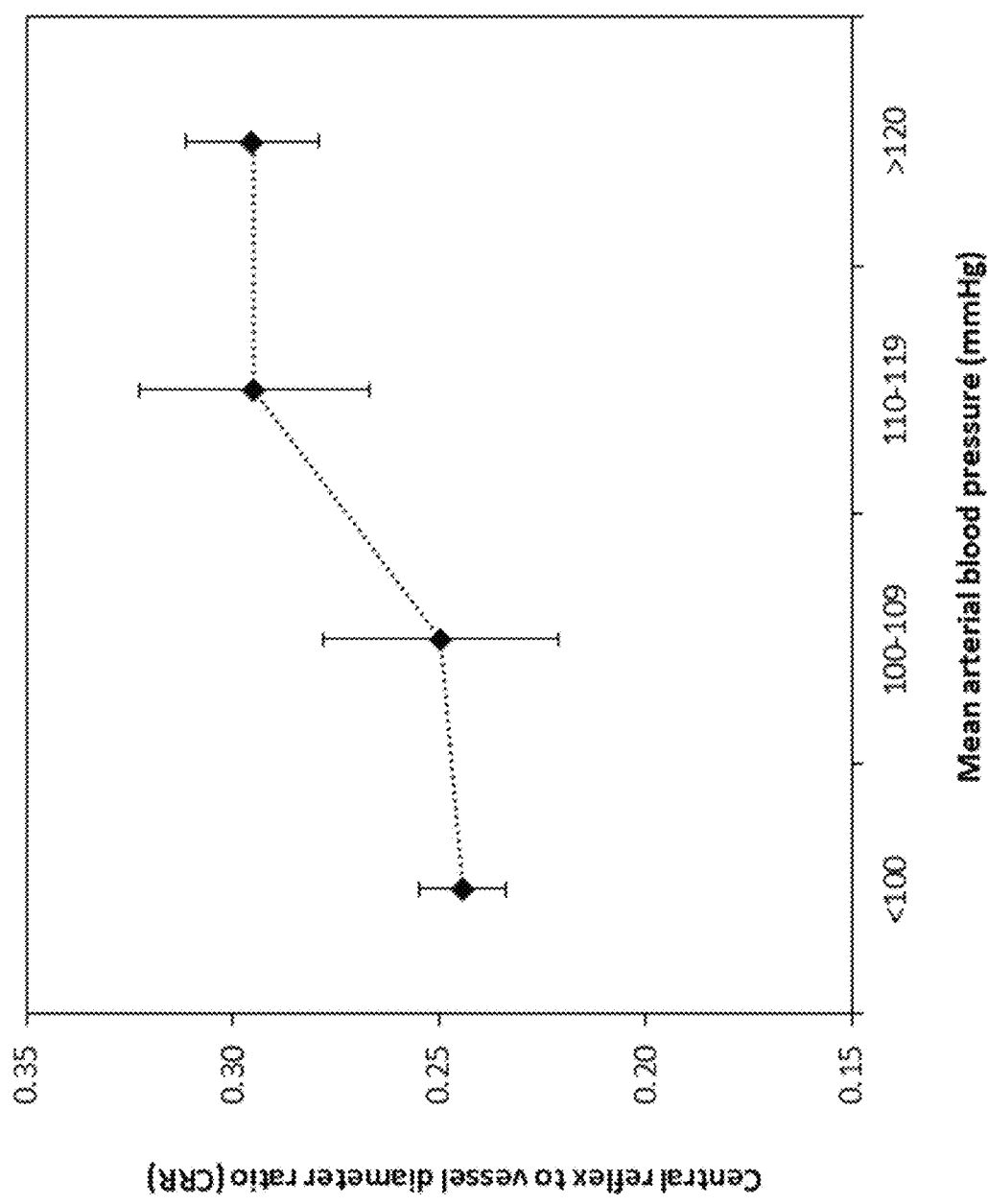
FIG. 14 is a graph showing the relationship, between a ratio of central reflex and blood vessel diameters and mean arterial blood pressure adjusted for age, body mass index, blood glucose, C-reactive protein and spherical equivalent (p-trend<0001).

In a multiple regression model adjusting for age, gender, body mass index, blood glucose, C-reactive protein and spherical equivalent, elevated mean arterial blood pressure was independently associated with higher CRR. Results of the multiple regression analysis are shown in Table 3 and FIG. 14.

TABLE 3

| | B | 95% CI | | Standardized β | p-value |
|---|---|---|---|---|---|
| Age | 0.00042 | −0.001 | 0.002 | 0.059 | 0.491 |
| Gender | 0.005 | −0.011 | 0.021 | 0.048 | 0.546 |
| Mean arterial ABP (per 10 mmHg increase) | 0.017 | 0.010 | 0.024 | 0.442 | <0.001 |
| BMI (per SD increase) | 0.001 | −0.008 | 0.010 | 0.012 | 0.838 |
| Blood Glucose (per SD increase) | 0.002 | −0.006 | 0.010 | 0.033 | 0.683 |
| C-reactive protein (per SD increase) | 0.002 | −0.007 | 0.011 | 0.041 | 0.616 |
| Spherical equivalent (per SD increase) | −0.003 | −0.012 | 0.005 | −0.063 | 0.460 |
| R square | 0.254 | | | | |

Accordingly, the above data demonstrate that the method for quantifying CR has good reliability and also that elevated blood pressure is significantly associated with higher CRR, hence indicating a link between retinal vascular changes and hypertension.

Previous studies of CR grading performed qualitative assessments, with reproducibility representing a major limitation. For example, previous studies reported that the graders' subjective assessment for the reproducibility for artery-vein nicking (a similar assessment) was only 0.4. However, the use of a computer assisted quantification approach results in significant improvements. In this regard, a major challenge to extract quantitative central reflex calibre is the fuzziness of the vessel edge and the accuracy of its detection for calibre measurement. For this reason, a semi-automated approach is particularly advantageous as it allows all the possible edge combinations within the region of interest to be considered. The grading interface also allows the grader to edit the detected artery and CR calibre to minimize the standard deviation in the measured widths. These techniques can be used to provide high reliability and repeatability of retinal arteriolar central reflex measurement which should thus provide enhanced information to find a higher confidence level or probability of association between CR and systemic diseases.

Visible broadening of the light reflex from retinal arterioles has also been found to be associated with atherosclerosis. The CR quantification system, with improved grading accuracy compared to the qualitative assessment, can benefit studies such as enhanced arteriolar light reflex sign and systemic vascular diseases, including hypertension and coronary artery disease. This quantified CRR allows the CR to be used as a biomarker for clinical practice with risk stratification and identification of individuals for vascular diseases.

Additionally, the CR measurement method can be sued to quantify retinal microvascular abnormalities in particular to quantify hypertensive retinopathy signs, in addition to current retinal vascular parameters (e.g. retinal vessel diameter), for assessment of retinal microcirculation. For example, current available CVD risk prediction tools, such as Framingham risk equations, can only detect CVD cases with 50% accuracy. It is thus clear that there is still a need in clinical practice for further markers of risk stratification and identification of persons at risk of hypertension and CVD. Quantification of arteriole and venular calibers can be used to assess generalized narrowing and its association with hypertension and cardiovascular disease (CVD). CR measurement is therefore a useful maker for assessing CVD risk as hypertensive retinopathy has long been regarded as a risk indicator for systemic morbidity and mortality.

Thus, the above described methods allow for quantification of the retinal central light reflex and demonstrated its reliability and validity and agreement against the current gold-standard manual method. This also demonstrates that a quantitative and reliable assessment of retinal arteriolar wall opacification is possible and can be used to assess for microvasculature and systemic diseases such as hypertension.

A further study was performed to investigate the retinal arteriolar central reflex in 123 healthy elderly (age 71.6±5.6 yrs., 55 male, 68 female) participants, and an additional cohort of 25 participants with Alzheimer's disease (AD) (age 72.4±7.5 yrs, 12 male, 13 female). As previously mentioned, the central reflex (CR) may provide information about vascular composition such as vessel wall opacification, and hence could be useful to detect or monitor microvascular changes mirroring those in cerebrovascular disease.

The Apolipoprotein E (APOE) gene was considered in this study because the APOE ε4 allele is the largest genetic risk factor for Alzheimer's disease (AD) and is also associated with various forms of cardiovascular disease (CVD). The APOE gene has three codominant alleles (ε2, ε3, ε4) which code for six APOE phenotypes. These phenotypes are involved in cholesterol transport and the ε4 allele is associated with higher levels of total and low-density cholesterol. The link with CVD is believed to involve the influence of APOE on lipid metabolism and large-vessel atherosclerosis (vessel hardening). However, whether the APOE gene has similar effects on small vessels or microvasculature is less clear. The APOE ε4 allele has been found to associate with cerebral white matter lesions which are manifestations of cerebral microvascular disease. Hence it is possible that APOE alleles may influence disease processes at the microvascular level, and if this extends to both the brain and retina then the retina may provide a window through which to monitor cerebrovascular health.

The current study examined retinal arteriolar central reflex, in AD and healthy control participants and carriers and non-carriers of the APOE ε4 allele. Since other retinal vascular changes have been reported in AD, CR was also explored as a marker of AD and/or its risk factors including the APOE ε4 allele, CVD and hypertension.

Participants were neuroimaged for the presence of fibrillar brain amyloid using positron emission tomography (PET) with Pittsburgh Compound B (PiB). Results for neocortical standardized uptake value ratio (SUVR) were calculated and a bimodal distribution of PiB-PET SUVR values was observed in the HC group. Consequently, hierarchical cluster analysis yielded a cut-off for neocortical SUVR of 1.5, separating high from low plaque burden. Subjects were classified as PiB negative (HC−) if their neocortex SUVR was below 1.5, and PiB positive (HC+) if their neocortex SUVR was above 1.5.

Retinal photographs were examined by an experienced ophthalmologist for the presence of copper or silver wire vessels (mild or marked enhancement of the retinal arteriolar central reflex). This determination is subjective, although clinical guidelines define silver wiring as the presence of a CR with a sharp margin, less than one third of the width of the arteriolar vessel and consistently present over at least two thirds of the length of the arteriolar sector. Copper wiring is defined as presence of a CR with width greater than one third of the arteriole width, consistently present over at least two thirds of the length of the arteriolar sector.

The quantification techniques described above were also applied to calculate the size of the CR relative to the size of the retinal vessel, for the largest retinal arteriole in each retinal photograph, which were then used to compare the vessels of AD and HC participants. and HC− and HC+ participants, as well as to compare to the expert graders' assessment The data from this study were analysed using a variety of statistical methods that were deemed appropriate for the hypotheses tested. All statistical analyses were conducted in XLstat 2011 (Microsoft Excel). Normality of distribution was tested using the Shapiro-Wilk test and visual inspection of variable histograms (and visual inspection of residuals from linear regression analyses). Descriptive data analyses were undertaken to determine the means and standard deviations (SD) for the full cohort and each group.

Demographic comparisons were performed using a $\chi^2$ test for categorical variables (gender, hypertension, diabetes, smoking status and APOE ε4 status), and analysis of variance (ANOVA) for the continuous age variable ($p<0.05$ considered significant). Across-group ocular measures were compared using analysis of covariance (ANCOVA), correcting for confounders. Confounders considered for the retinal measures were age, gender, hypertension, diabetes, smoking status and APOE ε4 status). Confounders considered for the pupil measures were age, gender and APOE ε4 status. The likelihood of false positive results was minimised by adjusting p values according to the Benjamini and Hochberg false, discovery rate (FDR) method.

Receiver-operating characteristic (ROC) curve analysis was also performed to further illustrate the classification accuracy of the ocular measures. The area under the curve (AUC) of the ROC curves was calculated; an AUC of 1 indicates perfect classification ability into AD or HC, whereas an AUC near 0.5 indicates poor (random) classification ability. Logistical models combining ocular measures were created to assess combined classification performance.

A bimodal distribution of PiB SUVR was observed in the HC group of the full study. Consequently, to identify a PiB cutoff, analysis was performed on all elderly HC research participants (n=118, age 73.2±7.4 years) using a hierarchical cluster analysis that yielded a cutoff of 1.5 for neocortical SUVR. Subjects were classified as PiB negative if their neocortex SUVR was below 1.5, and PiB positive if their neocortex SUVR was above or equal to 1.5.

All AD and MCI participants in the ocular neuroimaging cohorts tested positive to elevated plaque burden, hence the groups considered for ANCOVA analysis were HC−, HC+, MCI+ and AD+, with the sign indicating testing positive or negative for elevated plaque burden. Unmatched HC−, HC+, MCI+ and AD+ groups were compared using standard ANCOVA models with Benjamini and Hochberg false discovery rate adjustment.

Linear regression, adjusted for the above confounders, was used to model the relationship between retinal parameters and SUVR for the HC+ group and change in SUVR over the 18 month period prior to ocular testing for all 30 HC participants. Statistical significance was defined as $p<0.05$.

For the clinician-graded results, the healthy cohort consisted of 123 participants, of which 38 were APOE ε4 carriers. Silver wiring was not reported in either group but copper wiring was common in both groups. The APOE ε4 allele was not found to associate with copper or silver wiring retinopathy, arterio-venular (AV) nicking or focal arteriolar narrowing. Accordingly, this proved to be of little value from a discriminatory perspective.

An additional cohort of 25 probable-AD patients was included to compare to the 123 healthy control participants. The AD group had a higher percentage of APOE ε4 carriers (p=0.019) and reduced HDL cholesterol levels (p=0.042). Silver wiring was not reported in either group but copper wiring was common in both groups. AD diagnosis was not associated with copper or silver wiring, retinopathy, arterio-venular (AV) nicking or focal arteriolar narrowing and again this proved to be of little value from a discriminatory perspective.

For analysis of Central Reflex using the above described techniques, 112 of the 123 participants had photographs gradable by automated analysis in at least 1 eye. The cohort included 38 APOE ε4 carriers and 76 non-carriers. APOE ε4 carrier and non-carrier groups did not differ significantly in age, gender, mean arterial blood pressure hypertension, diabetes, smoking status, previous cataract surgery or cholesterol (HDL or LDL). A strong association between the APOE ε4 allele and CRR was found (p=0.0003), although the APOE ε4 allele did not associate individually with CR or arteriolar width. In a stepwise ANCOVA analysis for CRR, including confounders, only the APOE ε4 allele variable was retained (p=0.0003, $R^2$=0.108, DF=114.0. F=13.855, Pr>F=0.0003).

Again the additional cohort of probable-AD patients was included to compare to the healthy individuals, 22 of 25 (88%) had photographs gradable by automated analysis in at least 1 eye. AD and HC groups did not differ significantly in age, gender, hypertension, diabetes, smoking status, previous cataract surgery, APOE ε4 carriers or LDL cholesterol, however HDL cholesterol was lower in the AD group. The central reflex to vessel width ratio (CRR) for the largest arteriole was higher in AD based on ANOVA analysis (p=0.018, std coef=0.20, std error=0.09). However, in an ANCOVA model for CRR including confounders and AD status, with stepwise removal for p>0.1, only AD status (p=0.056, std coef=0.16, std error=0.08) and APOE ε4 carrier (p<0.0001, std coef=0.34, std error=0.08) were retained (model $R^2$=0.154, DF=2, F=11.889, p<0.0001), indicating that CRR is very strongly related to APOE ε4 status but exhibits only a weaker, independent trend with AD. However, it will also be appreciated that use of CR quantification and in particular determination of CRR provided a significant discriminatory capability compared to visual assessment.

In any event, a strong association was found between the APOE ε4 allele and larger retinal CRR as measured through quantification of CRR. This result adds to the evidence that firstly, the APOE ε4 allele may influence disease processes at the microvascular level, and secondly, that retinal photography and the CRR measure can detect microvascular changes of clinical significance. With the APOE ε4 allele already linked to Alzheimer's disease and cerebral white matter lesions disease, it seems that this gene might exert microvascular influence in both retina and brain simultaneously, allowing non-invasive retinal photography to act as a monitor for retinal and cerebral microvascular health.

CRR was also graded subjectively by a clinician, as either normal, copper wiring or silver wiring. While no participants were graded as having silver wiring, copper wiring was highly prevalent. No relationship between copper wiring and APOE ε4 status was found, but a non-significant trend for greater prevalence of copper wiring in AD was found. The reason that only the quantification technique found a robust association between CRR and APOE ε4 status appears to be the more detailed quantification of CRR provided by this technique. It seems that most individuals in the demographic concerned exhibit some level of enhanced CRR, and that this quantification technique shows potential for more accurate probing of CRR changes through quantification of the CRR rather than simply reporting copper wiring.

Thus, the above demonstrates a strong association between APOE ε4 carrier status and retinal CRR allowing CRR to be used for non-invasive monitoring of the effects of APOE ε4 on the central nervous system, particularly in cerebrovascular disease.

The term subject includes any living system, and in particular can include human, or non-human subjects. Thus, whilst the above examples have focussed on a subject such as a human, it will be appreciated that the apparatus and techniques described above can be used with any animal, including but not limited to, primates, livestock, performance animals, such as race horses, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method for quantifying a blood vessel reflection parameter associated with a biological subject, the method including, in at least one electronic processing device:
   a) determining, from a fundus image of an eye of the subject, edge points of at least one blood vessel in a region near an optic disc;
   b) processing the fundus image, at least in part using the edge points, to identify blood vessel edges and central reflex edges;
   c) determining blood vessel and central reflex parameter values using the blood vessel edges; and,
   d) determining a blood vessel reflection parameter value at least partially indicative of blood vessel reflection using the blood vessel and central reflex parameter values.

2. The method according to claim 1, wherein the blood vessel and central reflex parameter values are indicative of blood vessel and central reflex diameters respectively.

3. The method according to claim 1, wherein the blood vessel reflection parameter is based on a ratio of the blood vessel and central reflex parameters.

4. The method according to claim 1, wherein the region is an annular region surrounding the optic disc.

5. The method according to claim 1, wherein the method further includes:
   determining an optic disc location;
   determining an extent of the optic disc at least in part using the optic disc location; and,
   determining the region using the extent of the optic disc.

6. The method according to claim 5, wherein the method further includes determining the optic disc location by:
   displaying the at least one fundus image to a user; and,
   determining the optic disc location in accordance with user input commands.

7. The method according to claim 1, wherein the method further includes:
   displaying an indication of the region to the user; and,
   determining the edge points in accordance with user input commands.

8. The method according to claim 1, wherein the method includes processing the fundus image by:
   rotating the fundus image so that the blood vessel extends substantially across the fundus image; and,
   cropping the fundus image to remove parts of the fundus image beyond an extent of the edge points.

9. The method according to claim 1, wherein the method further includes:
   identifying potential edges in the fundus image using an edge detection algorithm;
   selecting edges from the potential edges using an edge selection algorithm.

10. The method according to claim 1, wherein the method further includes:
    identifying outer edges as blood vessel edges; and,
    determining edges between the blood vessel edges to be potential central reflex edges.

11. The method according to claim 10, wherein the method further includes selecting central reflex edges from the potential central reflex edges based on changes in image intensity.

12. The method according to claim 1, wherein the method further includes:
    determining a plurality of blood vessel and central reflex diameters using the blood vessel and central reflex edges; and,
    determining the blood vessel and central reflex parameter values using the plurality of blood vessel and central reflex diameters.

13. The method according to claim 12, wherein the method further includes at least one of:
    determining the plurality of blood vessels and central reflew diameters using opposite edge points of edge pixel pairs; and
    determining the blood vessel and central reflex parameter values by at least one of:

i) selecting a minimum diameter; and;
ii) determining an average diameter.

14. The method according to claim 1, wherein the method further includes, determining a blood vessel profile using blood vessel reflection parameter values for a plurality of blood vessels in the region.

15. The method according to claim 1, wherein at least one of a blood vessel reflection parameter value and a blood vessel profile are used as a biomarker for predicting at least one of:
i) vascular disease;
ii) cerebrovascular disease;
iii) APOE ϵ4 status; and,
iv) Alzheimer's disease.

16. The method according to claim 1, wherein the method further includes at least one of:
receiving the fundus image from a fundus camera;
receiving the fundus image from a remote computer system via a communications network; and,
retrieving the fundus image from a database.

17. A method for quantifying blood vessel reflection associated with the retina comprising:
a) selecting edge start-points of a suitable blood vessel around the optic disc area of a digital image of the eye fundus to constitute the edge start points for grading calculations;
b) automatically region cropping to create a cropped digital image around the edge start points and translating the cropped digital image to create a resultant image appropriately orientated for processing;
c) processing the resultant image digitally to obtain blood vessel edge and central reflex edge information from the identified vessel edges; and
d) measuring the calibres of the outer edges of the blood vessel and the central reflex from the edge information.

18. The method as claimed in claim 17, further including calculating the vessel reflection index being the ratio of the blood vessel calibre and the central reflex calibre to constitute a biomarker for predicting vascular disease of a patient.

19. A blood vessel quantification system for quantifying blood vessel reflection associated with the retina comprising:
a) a user interface for enabling an analyst to interact with the system;
b) an optic disc (OD) selection process for automatically computing an OD area and a vessel selection (VS) area after the analyst defines the OD centre on the digital image of the fundus using the user interface;
c) a mapping, processing and measuring (MPM) process including:
i) an image region selection process for automatically mapping a proximal region around vessel edge start-points and obtaining a selected image for subsequent processing;
ii) an edge detection and profiling process for automatically processing the selected image to obtain and map the vessel edge and central reflex edge profiles;
iii) an edge selection process for automatically selecting vessel edges and central reflex edges closest to the vessel edge start-points to calculate the calibre of the outer vessel edges and the central reflex edges; and
iv) a vessel reflection index measurement process for automatically calculating the vessel refection index of the selected vessel;
wherein the MPM process includes a vessel edge selection process for interactively functioning with the analyst via the user interface to enable the analyst to set the vessel edge start-points from within the VS area after the OD selection process has completed computing the VS area for the MPM process to proceed with performing the aforementioned automated processes.

20. The system as claimed in claim 19, wherein the user interface includes a module to allow an analyst to select an image file containing a digital image of the fundus of the eye of a patient, and enter relevant reference data for subsequent processing by the system.

* * * * *

UNITED STATES PATENT AND TRADEMARK OFFICE
CERTIFICATE OF CORRECTION

PATENT NO. : 9,848,765 B2  
APPLICATION NO. : 14/903751  
DATED : December 26, 2017  
INVENTOR(S) : Yogesan Kanagasingam and Alauddin Bhuiyan It is certified that error appears in the above-identified patent and that said Letters Patent is hereby corrected as shown below:

On the Title Page

In Column 1, (73) Assignee, delete "Industrail", and insert therefor --Industrial--.

In the Claims

In Claim 13, Column 24, Line 64, delete "reflew" and insert therefor --reflex--.

In Claim 19, Column 26, Line 24, delete "refection" and insert therefor --reflection--.

Signed and Sealed this  
Twentieth Day of March, 2018

Andrei Iancu  
*Director of the United States Patent and Trademark Office*